(12) United States Patent
Bhattacharjee et al.

(10) Patent No.: US 11,471,512 B2
(45) Date of Patent: Oct. 18, 2022

(54) PHARMACEUTICAL COMPOSITIONS OF A PEPTIDE

(71) Applicant: Merck Sharp & Dohme Corp., Rahway, NJ (US)

(72) Inventors: Himanshu Bhattacharjee, Collegeville, PA (US); Suzanne M. D'Addio, Jamaica Plain, MA (US); Sachin Lohani, Annandale, NJ (US); Sachin Mittal, Bridgewater, NJ (US); Sergei Y. Pechenov, Gaithersburg, MD (US); Daniel Hong Yin, Exton, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 16/801,227

(22) Filed: Feb. 26, 2020

(65) Prior Publication Data
US 2020/0276274 A1    Sep. 3, 2020

Related U.S. Application Data

(60) Provisional application No. 62/812,375, filed on Mar. 1, 2019.

(51) Int. Cl.

| | | |
|---|---|---|
| *A61K 38/00* | (2006.01) | |
| *A61K 38/26* | (2006.01) | |
| *A61K 47/10* | (2017.01) | |
| *A61K 47/18* | (2017.01) | |
| *A61K 47/22* | (2006.01) | |
| *A61K 47/26* | (2006.01) | |
| *A61K 47/24* | (2006.01) | |

(52) U.S. Cl.
CPC .............. *A61K 38/26* (2013.01); *A61K 47/10* (2013.01); *A61K 47/183* (2013.01); *A61K 47/186* (2013.01); *A61K 47/22* (2013.01); *A61K 47/24* (2013.01); *A61K 47/26* (2013.01)

(58) Field of Classification Search
CPC ...... A61K 38/26; A61K 47/10; A61K 47/183; A61K 47/186; A61K 47/22; A61K 47/24; A61K 47/26; A61K 9/0019; A61P 3/10
See application file for complete search history.

(56) References Cited

U.S. PATENT DOCUMENTS

| | | | |
|---|---|---|---|
| 8,114,833 B2 | 2/2012 | Pedersen et al. | |
| 2012/0283179 A1* | 11/2012 | Brunner-Schwarz | ....................... A61K 47/20 514/5.3 |
| 2016/0067184 A1* | 3/2016 | Nielsen | ..................... A61P 3/04 514/5.3 |
| 2018/0333493 A1* | 11/2018 | Shenoy | ................ C07K 16/241 |

FOREIGN PATENT DOCUMENTS

| | | | | |
|---|---|---|---|---|
| EP | 2498801 A1 * | 9/2012 | ........... | A61K 31/198 |
| WO | 2009155258 A2 | 12/2009 | | |
| WO | WO2010096052 A1 | 8/2010 | | |
| WO | WO2010096142 A1 | 8/2010 | | |
| WO | 2012177443 A2 | 12/2012 | | |
| WO | WO-2017210100 A1 * | 12/2017 | ........... | A61K 31/197 |

OTHER PUBLICATIONS

English language translation of EP 2498801 obtained by Google patents (Year: 2018).*
Alford, John R. et al., Effect of Benzyl Alcohol on Recombinant Human Interleukin-1 Receptor Antagonist Structure and Hydrogen-Deuterium Exchange, Journal of Pharmaceutical Sciences, 2011, 4215-4224, 100(10).
Bis, Regina L. et al., Antimicrobial preservatives induce aggregation of interferon alpha-2a: The order in which preservatives induce protein aggregation is independent of the protein, Int. J. Pharm., 2014, 356-361, 472.
Heljo, P. et al., Antimicrobial preservatives induce aggregation of interferon alpha-2a: The order in which preservatives induce protein aggregation is independent of the protein, Pharm. Res., 2015, 3201-3212, 32.
Hutchings, Regina L. et al., Effect of Antimicrobial Preservatives on Partial Protein Unfolding and Aggregation, Journal of Pharmacueitcal Sciences, 2013, 365-376, 102(2).
Maa, Yuh-Fun et al., Aggregation of recombinant human growth hormone induced by phenolic compounds, International Journal of Pharmaceutics, 1996, 155-168, 140.

* cited by examiner

*Primary Examiner* — Aradhana Sasan
*Assistant Examiner* — Mercy H Sabila
(74) *Attorney, Agent, or Firm* — Baerbel R. Brown; Catherine D. Fitch

(57) ABSTRACT

Disclosed are pharmaceutical compositions comprising the peptide of SEQ ID No. 1, or a pharmaceutically acceptable salt or counterion thereof, methods of preparing such pharmaceutical compositions, and methods of treating diabetes and diabetes-related disorders with such pharmaceutical compositions.

21 Claims, No Drawings

Specification includes a Sequence Listing.

SEQUENCE LISTING

```
<160> NUMBER OF SEQ ID NOS: 1

<210> SEQ ID NO 1
<211> LENGTH: 31
<212> TYPE: PRT
<213> ORGANISM: Artificial Sequence
<220> FEATURE:
<223> OTHER INFORMATION: Peptide 1
<220> FEATURE:
<221> NAME/KEY: MOD_RES
<222> LOCATION: (2)..(2)
<223> OTHER INFORMATION: Xaa is 2-aminoisobutyric acid
<220> FEATURE:
<221> NAME/KEY: MOD_RES
<222> LOCATION: (10)..(10)
<223> OTHER INFORMATION: Xaa is gamma-Glu-gamma-Glu-C16
<220> FEATURE:
<221> NAME/KEY: MOD_RES
<222> LOCATION: (16)..(16)
<223> OTHER INFORMATION: Xaa is 2-aminoisobutyric acid
<220> FEATURE:
<221> NAME/KEY: MOD_RES
<222> LOCATION: (31)..(31)
<223> OTHER INFORMATION: Xaa is gamma-Glu-amide

<400> SEQUENCE: 1

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Met Asn Thr Lys Xaa
            20                  25                  30
```

PHARMACEUTICAL COMPOSITIONS OF A PEPTIDE

CROSS-REFERENCE TO RELATED APPLICATIONS

This U.S. Non-provisional application claims priority from and the benefit of U.S. Provisional Application No. 62/812,375, filed Mar. 1, 2019.

REFERENCE TO SEQUENCE LISTING SUBMITTED ELECTRONICALLY

The sequence listing of the present application is submitted electronically via EFS-Web as an ASCII formatted sequence listing with a file name "24707USNPSEQLIST-26FEB2020.txt", creation date of Feb. 26, 2020, and a size of 1.07 KB. This sequence listing submitted via EFS-Web is part of the specification and is herein incorporated by reference in its entirety.

BACKGROUND OF THE INVENTION

Type 2 diabetes is a chronic and progressive disease arising from a complex pathophysiology involving the dual endocrine defects of insulin resistance and impaired insulin secretion. The treatment of Type 2 diabetes typically begins with diet and exercise, followed by oral or injectable anti-diabetic monotherapy. Many patients with type 2 diabetes are considered to be at high risk for coronary artery disease and associated co-morbidities. To reduce the risk of coronary artery disease, it is crucial to manage the entire risk spectrum. Treatment with cholesterol synthesis inhibitors in patients with and without coronary heart disease, including coronary artery disease, reduces the risk of cardiovascular morbidity and mortality.

Pre-pro glucagon is a 158 amino acid precursor polypeptide that is processed in different tissues to form pro-glucagon derived peptides, including glucagon, glucagon-like peptide-1 (GLP-1), glucagon-like peptide 2 (GLP-2) and oxyntomodulin (OXM), which are involved in glucose homeostasis, insulin secretion, gastric emptying, intestinal growth, and food intake regulation. Glucagon is a 29 amino acid peptide that corresponds to amino acids 33 through 61 of pre-proglucagon. GLP-1 is produced as a 37 amino acid peptide that corresponds to amino acids 72 through 108 of pre-proglucagon. GLP-1(7-36) amide and GLP-1(7-37) acid are biologically potent forms of GLP-1 with activity at the GLP-1 receptor.

Hypoglycemia is a common side effect of insulin therapy in patients with hyperglycemia (elevated blood glucose levels) due to diabetes. During hypoglycemia, when blood glucose levels drop below normal, glucagon signals the liver to break down glycogen and release glucose resulting in a blood glucose level rise toward a normal level. Glucagon's role in glucose regulation is to counteract the action of insulin and maintain normal blood glucose levels.

GLP-1's biological actions include stimulation of insulin synthesis and secretion, inhibition of glucagon secretion, and inhibition of food intake. GLP-1 has been shown to reduce hyperglycemia in diabetics. Likewise, exendin-4, a peptide from lizard venom, activates the GLP-1 receptor and has been shown to reduce hyperglycemia in diabetics. There is also evidence that GLP-1 and exendin-4 may reduce food intake and promote weight loss, which may be beneficial for diabetics and patients with obesity. Patients with obesity have a higher risk of diabetes, hypertension, hyperlipidemia, cardiovascular disease, and musculoskeletal diseases.

The peptide of SEQ. ID NO. 1 is a GLP-1/glucagon receptor co-agonist useful for treating diseases associated with agonism of the GLP-1 receptor and the glucagon receptor, such as type 2 diabetes.

The peptide of SEQ. ID NO. 1 has the following structural formula:

HUQGTFTSD K(γGlu-γGlu-C16) SKYLD aibRAAQDFVQWLMNTKγGlu-amide, wherein U is 2-aminoisobutyric acid, and C16=palmitoyl.

The peptide of SEQ. ID NO. 1, and pharmaceutically acceptable salts thereof, are disclosed in international patent publications WO 2009/155258, WO 2010/096142, WO 2010/096052, and WO 2012/177443.

The present invention comprises pharmaceutical compositions of the peptide of SEQ. ID NO. 1, or a pharmaceutically acceptable salt or counterion thereof, which provide for accurate single and multiple injection dosing in a stable peptide formulation that reduces the amount of oligomer formation.

SUMMARY OF THE INVENTION

Novel pharmaceutical compositions comprising The peptide of SEQ. ID NO. 1, or pharmaceutically acceptable salts thereof, are disclosed. The pharmaceutical compositions of the present invention are constituted into a solution by adding water prior to dosing to patients.

The pharmaceutical compositions of the present invention provide for the immediate release of the peptide of SEQ ID No. 1, or a pharmaceutically acceptable salt or counterion thereof.

The present invention also provides a process for the preparation of pharmaceutical compositions of the peptide of SEQ. ID NO. 1, or pharmaceutically acceptable salts thereof.

Another aspect of the present invention provides methods for the treatment of diabetes, or a diabetes-related disorder, by administering to a host in need of such treatment a therapeutically effective amount of a pharmaceutical composition of the peptide of SEQ ID No. 1, or a pharmaceutically acceptable salt or counterion thereof.

These and other aspects will become readily apparent from the detailed description which follows.

DETAILED DESCRIPTION OF THE INVENTION

The present invention is directed to pharmaceutical compositions of the peptide of SEQ. ID NO. 1, or a pharmaceutically acceptable salt or counterion thereof. The pharmaceutical compositions may be ready for constitution with water or as a ready to use solution for use in syringes or pen devices. The preparation of the peptide of SEQ. ID NO. 1, and pharmaceutically acceptable salts thereof, is disclosed in WO 2012/177443. Formulations of a GLP-1 agonist are described in U.S. Pat. No. 8,114,833. Anti-microbial preservative selection is described in: V. V. Maa et al, Int. J. Pharmaceut. 140, 155-168 (1996); J. R. Alford et al., J. Pharm. Sci., 100, 4215-4224; R. L. Hutchings et al., J. Pharm. Sci-US, 102, 365-376 (2013); R. L. Bis et al., Int. J. Pharmaceut., 472, 356-361 (2014); and P. Heljo et al., Pharm. Res-Dordr., 32, 3201-3212 (2015). The following patent relates to GLP-1 formulations: U.S. Pat. No. 8,114,833.

The peptide of SEQ ID NO. 1 has poor water solubility between pH 4 and pH 6, and poor chemical stability above pH 7.6. The major degradation pathways in aqueous formulations are de-amidation at high pH, isomerization and oxidation. Once dissolved in aqueous media, the peptide of SEQ ID NO. 1 has been shown to self-associate or self-aggregate into multimer and higher order species, or oligomers, depending on the solution conditions, such as changes in pH, temperature, ionic strength, and the type and amount of excipients.

Benzyl alcohol works as an anti-microbial agent to decrease bacterial and fungal load. However, it was unexpectedly found in the present invention that benzyl alcohol also works to solubilize and to improve the physical stability of the peptide of SEQ. I.D. No. 1. Benzyl alcohol works as a solubilizer in the formulation once constituted with water by increasing the solubility of the peptide of SEQ ID No. 1 and by preventing the peptide from precipitating out of solution. It was further unexpectedly found that benzyl alcohol improves the physical stability of peptide of SEQ ID No. 1 in the formulation once constituted with water by limiting peptide self-aggregation. During the development of the formulation of the peptide of SEQ ID NO. 1, it was unexpectedly discovered that the anti-microbial agents significantly influence the physical stability of the peptide. Near neutral pH, the addition of the anti-microbial agent phenol or m-cresol resulted in a hazy solution on addition of water due to due the self-association of higher order species of peptide, and subsequent precipitation of peptide. However, it was unexpectedly found that the addition of the anti-microbial agent benzyl alcohol limits the self-association or self-aggregation of the peptide of SEQ ID No. 1 to oligomers. Benzyl alcohol effectively prevents the formation of, dissociates, or solubilizes higher order peptide aggregates to provide the uniform solution needed for accurate dosing of peptide.

There is a need for a uniform, stable single and multi-dose formulation of the peptide of SEQ ID No. 1, in which peptide self-aggregation is limited.

To inhibit bacterial and mold and fungal growth in injectable solutions, an anti-microbial agent, such as phenol, m-cresol, benzyl alcohol, or benzalkonium chloride is commonly used. During the development of the present invention, it was found that upon addition phenol or m-cresol, the formulation became hazy upon addition of water, and the peptide self-aggregated. However, it was unexpectedly found that the addition of the anti-microbial agent benzyl alcohol increased the solubility of the peptide in the formulation upon addition of water resulting in a clear formulation solution in water. It was further unexpectedly found that the addition of the anti-microbial agent benzyl alcohol resulted in a decrease in peptide self-aggregation.

It was desirable to provide a solution formulation that exhibited minimal peptide precipitation and self-aggregation.

The present invention provides such a formulation. The present invention provides a composition of the peptide of SEQ. I.D. No. 1 for constitution with water that provides a formulation for single and multi-dose use with limited peptide precipitation and limited peptide self-aggregation.

The pharmaceutical compositions of the present invention comprise the peptide of SEQ ID No. 1, or a pharmaceutically acceptable salt or counterion thereof, and contain one or more of the following excipients: an anti-microbial agent, a buffer, an anti-oxidant, a tonicity agent, and optionally acid or base to adjust the pH provide for the formulation solution upon constitution with water.

In one embodiment of the present invention, the salt of the peptide of SEQ ID No. 1, is the acetate salt. In another embodiment of the present invention, the counterion of the peptide of SEQ ID No. 1 is the acetate counterion.

In another embodiment of the present invention, the peptide of SEQ ID No. 1, or a pharmaceutically acceptable salt or counterion thereof, is crystalline. In another embodiment, the peptide of SEQ ID No. 1, or a pharmaceutically acceptable salt or counterion thereof, is amorphous.

In another embodiment of the present invention, the pharmaceutical composition comprising the peptide of SEQ ID No. 1, or a pharmaceutically acceptable salt or counterion thereof, is constituted before administrating to the patient. In an class of this embodiment, the pharmaceutical composition is constituted with a solvent, a custom solvent or a custom diluent. In another class of this embodiment, the pharmaceutical composition is constituted with water. In another class of this embodiment, the pharmaceutical composition is constituted with a custom solvent. In a subclass of this class, the custom solvent is a saline solution or a 5% dextrose solution in water. In another class of this embodiment, the pharmaceutical composition is constituted with a custom diluent. In a subclass of this class, the custom diluent is the custom diluent of Example 2 or the custom diluent of Example 3.

In another embodiment of the present invention, the pharmaceutical composition comprising the peptide of SEQ ID No. 1, or a pharmaceutically acceptable salt or counterion thereof, additionally comprises a solvent. In a class of this embodiment, the solvent is water. In another embodiment of the present invention, the pharmaceutical composition comprising the peptide of SEQ ID No. 1, or a pharmaceutically acceptable salt or counterion thereof, additionally comprises a custom solvent. In a class of this embodiment, the custom solvent is a saline solution in water. In another class of this embodiment, the custom solvent is a 5% dextrose solution in water. In another embodiment of the present invention, the pharmaceutical composition comprising the peptide of SEQ ID No. 1, or a pharmaceutically acceptable salt or counterion thereof, additionally comprises a custom diluent. In a class of this embodiment, the custom diluent is the custom diluent of Example 2. In another class of this embodiment, the custom diluent is the custom diluent of Example 3.

In another embodiment of the present invention, a solvent is added to the pharmaceutical composition comprising the peptide of SEQ ID No. 1, or a pharmaceutically acceptable salt or counterion thereof, prior to injection. In a class of this embodiment, the solvent is water.

In another embodiment of the present invention, a custom solvent is added to the pharmaceutical composition comprising the peptide of SEQ ID No. 1, or a pharmaceutically acceptable salt or counterion thereof, prior to injection. In a class of this embodiment, the custom solvent is a saline solution or a 5% dextrose solution in water.

In another embodiment of the present invention, a custom diluent is added to the pharmaceutical composition comprising the peptide of SEQ ID No. 1, or a pharmaceutically acceptable salt or counterion thereof, prior to injection. In a class of this embodiment, the custom diluent is the custom diluent of Example 2. In another class of this embodiment, the diluent is the custom diluent of Example 3.

In another embodiment of the present invention, the pharmaceutical composition is a solution for injection comprising the peptide of SEQ ID No. 1, or a pharmaceutically acceptable salt or counterion thereof.

In another embodiment of the present invention, the pharmaceutical composition comprises the peptide of SEQ ID No. 1, or a pharmaceutically acceptable salt or counterion thereof, and the excipients to which water is added prior to injection.

In another embodiment of the present invention, the pharmaceutical composition comprises the peptide of SEQ ID No. 1, or a pharmaceutically acceptable salt or counterion thereof, and the excipients to which a custom solvent is added prior to injection. In a class of this embodiment, the custom solvent is a saline solution in water. In another class of this embodiment, the custom solvent is a 5% dextrose solution in water.

In another embodiment of the present invention, the pharmaceutical composition comprises the peptide of SEQ ID No. 1, or a pharmaceutically acceptable salt or counterion thereof, to which a custom diluent is added prior to injection. In a class of this embodiment, the custom diluent is the custom diluent of Example 2. In another class of this embodiment, the custom diluent is the custom diluent of Example 3.

In another embodiment of the present invention, the pharmaceutical composition contains 0.1 mg of the peptide of SEQ. I.D. No. 1. In a class of this embodiment, a solvent, a custom solvent or a custom diluent is added to the pharmaceutical composition to provide a 1 mL solution.

In another embodiment of the present invention, the pharmaceutical composition contains 0.2 mg of the peptide of SEQ. I.D. No. 1. In a class of this embodiment, a solvent, a custom solvent or a custom diluent is added to the pharmaceutical composition to provide a 1 mL solution In another embodiment of the present invention, the pharmaceutical composition contains 0.5 mg of the peptide of SEQ. I.D. No. 1. In a class of this embodiment, a solvent, a custom solvent or a custom diluent is added to the pharmaceutical composition to provide a 1 mL solution.

In another embodiment of the present invention, the pharmaceutical composition contains 1 mg of the peptide of SEQ. I.D. No. 1. In a class of this embodiment, a solvent, a custom solvent or a custom diluent is added to the pharmaceutical composition to provide a 2 mL solution.

In another embodiment of the present invention, the pharmaceutical composition contains 1.5 mg of the peptide of SEQ. I.D. No. 1. In a class of this embodiment, a solvent, a custom solvent or a custom diluent is added to the pharmaceutical composition to provide a 2 mL solution.

In another embodiment of the present invention, the pharmaceutical composition contains 2 mg of the peptide of SEQ. I.D. No. 1. In a class of this embodiment, a solvent, a custom solvent or a custom diluent is added to the composition to provide a 2 mL solution In another embodiment of the present invention, the pharmaceutical composition contains 2.5 mg of the peptide of SEQ. I.D. No. 1. In a class of this embodiment, a solvent, a custom solvent or a custom diluent is added to the pharmaceutical composition to provide a 3 mL solution .

In another embodiment of the present invention, the pharmaceutical composition contains 4 mg of the peptide of SEQ. I.D. No. 1. In a class of this embodiment, a solvent, a custom solvent or a custom diluent is added to the pharmaceutical composition to provide a 3 mL solution.

In another embodiment of the present invention, the pharmaceutical composition contains 10 mg of the peptide of SEQ. I.D. No. 1. In a class of this embodiment, a solvent, a custom solvent or a custom diluent is added to the pharmaceutical composition to provide a 3 mL solution.

In another embodiment of the present invention, the pharmaceutical composition additionally comprises a solvent. In a class of this embodiment, the solvent is added to obtain a 1 mL solution. In another class of this embodiment, the solvent is added to obtain a 2 mL solution. In another class of this embodiment, the solvent is added to obtain a 3 mL solution.

In another embodiment of the present invention, the pharmaceutical composition additionally comprises a custom solvent. In a class of this embodiment, the custom solvent is added to obtain a 1 mL solution. In another class of this embodiment, the custom solvent is added to obtain a 2 mL solution. In another class of this embodiment, the custom solvent is added to obtain a 3 mL solution.

In another embodiment of the present invention, the pharmaceutical composition additionally comprises a custom diluent. In a class of this embodiment, the custom diluent is added to obtain a 1 mL solution. In another class of this embodiment, the custom diluent is added to obtain a 2 mL solution. In another class of this embodiment, the custom diluent is added to obtain a 3 mL solution.

In another embodiment of the present invention, the pharmaceutical composition additionally comprises water. In a class of this embodiment, water is added to obtain a 1 mL solution. In another class of this embodiment, water is added to obtain a 2 mL solution. In another class of this embodiment, water is added to obtain a 3 mL solution.

In another embodiment of the present invention, the pH of the composition in a solvent, a custom solvent or a custom diluent is about pH 6.7 to about pH 8.4. In another embodiment of the present invention, the pH of the composition in a solvent, a custom solvent or a custom diluent is about pH 6.8 to about pH 7.6. In another embodiment of the present invention, the pH of the composition in water is about pH 6.9 to about pH 7.3. In another embodiment of the present invention, the pH of the composition in a solvent, a custom solvent or a custom diluent is about pH 7.1. In another embodiment of the present invention, the pH of the composition in a solvent, a custom solvent or a custom diluent is adjusted by the addition of a base and an acid. In a class of this embodiment, the base is sodium hydroxide. In another class of this embodiment, the base is 1 N sodium hydroxide. In another class of this embodiment, the acid is hydrochloric acid. In another class of this embodiment, the acid is 1N hydrochloric acid.

In another embodiment of the present invention, the pH of the composition in water is about pH 6.7 to about pH 8.4. In another embodiment of the present invention, the pH of the composition in water is about pH 6.8 to about pH 7.6. In another embodiment of the present invention, the pH of the composition in water is about pH 6.9 to about pH 7.3. In another embodiment of the present invention, the pH of the composition in water is about pH 7.1. In another embodiment of the present invention, the pH of the composition in water is adjusted by the addition of a base and an acid. In a class of this embodiment, the base is sodium hydroxide. In another class of this embodiment, the base is 1 N sodium hydroxide. In another class of this embodiment, the acid is hydrochloric acid. In another class of this embodiment, the acid is 1 N hydrochloric acid.

In another embodiment of the present invention, the pharmaceutical composition of the peptide of SEQ ID No. 1 comprises a solvent, and/or an anti-oxidant, and/or an anti-microbial agent, and/or a tonicity agent, and/or pH modifier.

In another embodiment of the present invention, the pharmaceutical composition of the peptide of SEQ ID No. 1 comprises a custom solvent, and/or an anti-oxidant, and/or an anti-microbial agent, and/or a tonicity agent, and/or pH modifier.

In another embodiment of the present invention, the pharmaceutical composition of the peptide of SEQ ID No. 1 comprises a custom diluent, and/or an anti-oxidant, and/or an anti-microbial agent, and/or a tonicity agent, and/or pH modifier.

In another embodiment of the present invention, the pharmaceutical composition of the peptide of SEQ ID No. 1 comprises water, and/or an anti-oxidant, and/or an anti-microbial agent, and/or a tonicity agent, and/or pH modifier.

In another embodiment of the present invention, the pharmaceutical composition may be used for subcutaneous injection of the peptide of SEQ ID No. 1, or a pharmaceutically acceptable salt or counterion thereof. In another embodiment, the pharmaceutical composition is a solution for injection administered via syringe or pen injection device. In another embodiment of the present invention, the composition is in the dosage form of a cartridge, vial or ready to use syringe. In a class of this embodiment, the composition is in the dosage form of a cartridge or vial to which water is added for constitution prior to injection.

In another embodiment of the present invention, the pharmaceutical compositions of the present invention are constituted by adding a precise volume of a solvent, a custom solvent or a custom diluent prior to dosing to patients. In a class of this embodiment, the solvent is water. In another class of this embodiment, the custom solvent is a saline solution, or a 5% dextrose solution in water. In another class of this embodiment, the custom diluent is the custom diluent of Example 2 or the custom diluent of Example 3.

The pharmaceutical composition of the present invention may be provided in a vial, cartridge, pen device or a syringe, such as a ready to use syringe. To ensure dose uniformity and accuracy, the solution must be homogeneous without peptide self-aggregation or peptide precipitation. In another embodiment of the present invention, the pharmaceutical composition comprising the peptide of SEQ ID NO. 1 may be administered by injection. In another embodiment of the present invention, the pharmaceutical composition comprising the peptide of SEQ ID NO 1 may be administered by subcutaneous injection. In another embodiment of the present invention, the pharmaceutical composition comprising the peptide of SEQ ID NO 1 may be administered by subcutaneous injection using a syringe or pen injector device.

Pharmaceutical compositions in solution are preferred IV dosage forms to administer peptides via subcutaneous injection in accurate and variable volumes dosed over multiple dosing intervals.

In another embodiment of the present invention, the multi-dose use corresponds to one or more doses per day over a 1-30 day interval. In another embodiment, the multi-dose use corresponds to one or more doses per day over a 7-14 day interval.

The pharmaceutical compositions of the present invention contain one or more anti-microbial agents. An acceptable anti-microbial agent or antimicrobial/antifungal agent approved for injectable use may be added to prevent proliferation or growth of bacteria, yeasts, fungi or molds in the constituted suspension formulation. Examples of anti-microbial agents include, but are not limited to: phenol, m-creosol, benzyl alcohol, phenoxyethanol, and benzalkonium chloride. In one embodiment of the present invention, the anti-microbial agent is selected from one or more of: phenoxyethanol, phenol, m-cresol, benzyl alcohol and benzalkonium chloride. In another embodiment of the present invention, the anti-microbial agent is selected from one or more of: phenol, m-cresol, benzyl alcohol and benzalkonium chloride. In another embodiment of the present invention, the anti-microbial agent is phenoxyethanol. In another embodiment of the present invention, the anti-microbial agent is phenol. In another embodiment of the present invention, the anti-microbial agent is m-creosol. In another embodiment of the present invention, the anti-microbial agent is benzyl alcohol. In another embodiment of the present invention, the anti-microbial agent is benzalkonium chloride.

The pharmaceutical compositions of the present invention contain one or more buffers. The term buffer means an agent that maintains the desired pH by providing sufficient buffer capacity to resist pH changes. The buffer is added to the pharmaceutical composition to ensure a solution pH at which the aqueous solubility of the peptide, or a pharmaceutically acceptable salt or counterion thereof, is relatively high. Buffers are also included to reduce variation in pH, and maintain pH to control chemical degradation by deamidation. Examples of buffers include, but are not limited to: phosphate (sodium phosphate and dibasic sodium phosphate dihydrate); tri(hydroxymethdyl)aminomethane (TRIS or THAM); L-histidine; citrate (sodium citrate); acetate (sodium acetate); lactate (lactic acid or sodium lactate); tartaric acid; and glycine. In one embodiment the buffer is buffer is selected from sodium phosphate, dibasic sodium phosphate dihydrate; tri(hydroxymethdyl)aminomethane (TRIS or THAM); or L-histidine. In another embodiment, the buffer is phosphate. In another embodiment, the buffer is sodium phosphate and dibasic sodium phosphate dihydrate. In another embodiment, the buffer is TRIS. In another embodiment, the buffer is THAM. In another embodiment, the buffer is L-histidine.

The pharmaceutical compositions of the present invention contain one or more anti-oxidants. Examples of anti-oxidants include, but are not limited to: L-methionine and ethylenediamine tetra acetic acid (EDTA), ascorbic acid, histidine, diethylenetriamine pentaacetate (DTPA), glutathione, sodium citrate, and ethanol. The pharmaceutical composition may include one or more anti-oxidants. In one embodiment of the present invention, the anti-oxidant is a combination of L-methionine and ethylenediamine tetra acetic acid (EDTA). In another embodiment of the present invention, the anti-oxidant is selected from L-methionine and ethylenediamine tetra acetic acid (EDTA). In another embodiment of the present invention, the anti-oxidant is L-methionine. In another embodiment of the present invention, the anti-oxidant is ethylenediamine tetra acetic acid.

The pharmaceutical compositions of the present invention contain one or more tonicity agent. Examples of tonicity agents include, but are not limited to: propylene glycol, glycine, proline, glutamate; salts including but not limited to sodium chloride, potassium chloride, and sodium sulfate; and non-reducing sugars, such as mono-saccharides and di-saccharides, including mannitol, glycerol, trehalose, sorbitol, and sucrose. In one embodiment of the present invention, the tonicity agent is present in sufficient quantity to provide a solution of the pharmaceutical composition with the appropriate osmolality for injection. In another embodiment of the present invention, the tonicity agent is selected from propylene glycol, mannitol, glycerol and sucrose. In another embodiment of the present invention, the tonicity agent is selected from: propylene glycol and sucrose. In another embodiment of the present invention, the tonicity agent is propylene glycol. In another embodiment of the present invention, the tonicity agent is mannitol. In another embodiment of the present invention, the tonicity agent is glycerol. In another embodiment of the present invention, the tonicity agent is sucrose.

The pharmaceutical composition of the present invention is dissolved in a solvent, or a custom solvent, or a custom diluent for injection. In one embodiment of the present invention, the pharmaceutical composition is dissolved in water-for-injection and the pH is adjusted with an acid and/or base to about pH 6.7 to 8.4. In another embodiment of the present invention, the pharmaceutical composition is dissolved in water-for-injection and the pH is adjusted with an acid and/or base to about pH 6.8 to 7.6. In another embodiment of the present invention, the pharmaceutical composition is dissolved in water-for-injection and the pH is adjusted with an acid and/or base to about pH 6.9 to 7.3. In another embodiment of the present invention, the pharmaceutical composition is dissolved in water-for-injection and the pH is adjusted with an acid and/or base to about pH 6.8. In another embodiment of the present invention, the pharmaceutical composition is dissolved in water-for-injection and the pH is adjusted with an acid and/or base to about pH 6.9.

In another embodiment of the present invention, the pharmaceutical composition is dissolved in a custom solvent-for-injection and the pH is adjusted with an acid and/or base to about pH 6.7 to 8.4. In another embodiment of the present invention, the pharmaceutical composition is dissolved in a custom solvent-for-injection and the pH is adjusted with an acid and/or base to about pH 6.8 to 7.6. In another embodiment of the present invention, the pharmaceutical composition is dissolved in a custom solvent-for-injection and the pH is adjusted with an acid and/or base to about pH 6.9 to 7.3. In another embodiment of the present invention, the pharmaceutical composition is dissolved in a custom solvent-for-injection and the pH is adjusted with an acid and/or base to about pH 6.8.

In another embodiment of the present invention, the pharmaceutical composition is dissolved in a custom diluent-for-injection and the pH is adjusted with an acid and/or base to about pH 6.9. In another embodiment of the present invention, the pharmaceutical composition is dissolved in a custom diluent for-injection and the pH is adjusted with an acid and/or base to about pH 6.7 to 8.4. In another embodiment of the present invention, the pharmaceutical composition is dissolved in a custom diluent for-injection and the pH is adjusted with an acid and/or base to about pH 6.8 to 7.6. In another embodiment of the present invention, the pharmaceutical composition is dissolved in a custom diluent for-injection and the pH is adjusted with an acid and/or base to about pH 6.9 to 7.3. In another embodiment of the present invention, the pharmaceutical composition is dissolved in a custom diluent for-injection and the pH is adjusted with an acid and/or base to about pH 6.8. In another embodiment of the present invention, the pharmaceutical composition is dissolved in a custom diluent-for-injection and the pH is adjusted with an acid and/or base to about pH 6.9.

In another embodiment of the present invention, the pharmaceutical composition is dissolved in water-for-injection and the pH is adjusted with an acid and/or base to about pH 7.0. In another embodiment of the present invention, the pharmaceutical composition is dissolved in water-for-injection and the pH is adjusted with an acid and/or base to about pH 7.1. In another embodiment of the present invention, the pharmaceutical composition is dissolved in water-for-injection and the pH is adjusted with an acid and/or base to about pH 7.2. In another embodiment of the present invention, the pharmaceutical composition is dissolved in water-for-injection and the pH is adjusted with an acid and/or base to about pH 7.3. In another embodiment of the present invention, the acid is hydrochloric acid. In another embodiment of the present invention, the base is sodium hydroxide.

The term "pH modifier" refers to the acid and/or base used to adjust the pH of the pharmaceutical composition of the present invention when dissolved in a solvent, or a custom diluent, or a custom diluent. In one embodiment the solvent is water. In another embodiment, the custom solvent is a saline solution or a 5% dextrose solution in water. In another embodiment, the custom diluent is the custom diluent of Example 2 or Example 3. Examples of pH modifiers include, but are not limited to, sodium hydroxide and hydrochloric acid.

The dose of the peptide of SEQ ID No. 1, or a pharmaceutically acceptable salt or counterion thereof, for incorporation into the pharmaceutical compositions of the present invention is an amount from about 5 micrograms per day to about 5000 micrograms per day of the active moiety. In another embodiment, the dose of the peptide of SEQ ID No. 1, or a pharmaceutically acceptable salt or counterion thereof, is an amount from about 10 micrograms per day to about 2000 micrograms per day of the active moiety. In another embodiment, the dose of the peptide of SEQ ID No. 1, or a pharmaceutically acceptable salt or counterion thereof, is an amount from about 50 micrograms per day to about 900 micrograms per day of the active moiety. In another embodiment, the dose of the peptide of SEQ ID No. 1, or a pharmaceutically acceptable salt or counterion thereof, is an amount from about 50 micrograms per day to about 600 micrograms per day of the active moiety.

Discrete doses, include but are not limited to, the equivalent of 10 µg, 40 µg, 50 µg, 70 µg, 100 µg, 130 µg, 150 µg, 170 µg, 200 µg, 230 µg, 250 µg, 270 µg, 280 µg, 300 µg 330 µg, 350 µg, 360 µg, 390 µg, 420 µg, 450 µg, 480 µg, 500 µg, 510 µg, 540 µg, 550 µg, 570 µg, 600 µg, 630 µg, 650 µg, 680 µg, 700 µg, 720 µg, 750 µg, 780 µg, 800 µg, 810 µg, 830 µg, 850 µg, 860 µg, 890 µg, 900 µg, 930 µg, 950 µg, 960 µg, 980 µg, 990 µg, 1000 µg, 1030 µg, 1050 µg, 1080 µg, 1200 µg, 1210 µg, 1250 µg, 1260 µg, 1290 µg, 1300 µg, 1310 µg, 1330 µg, 1350 µg, 1380 µg, 1400 µg, 1410 µg, 1430 µg, 1440 µg, 1450 µg, 1480 µg, 1500 µg, 1530 µg, 1550 µg, 1580 µg, 1600 µg, 1630 µg, 1650 µg, 1680 µg, 1700 µg, 1730 µg, 1750 µg, 1780 µg, 1800 µg, 1830 µg, 1850 µg, 1880 µg, 1900 µg, 1930 µg, 1950 µg, 1980 µg, 2000 µg, 2500 µg, 3000 µg, 3500 µg, 4000 µg, 4500 µg and 5000 µg of the peptide of SEQ ID No. 1, or a pharmaceutically acceptable salt or counterion thereof, per day. A preferred dose of the peptide of SEQ ID No. 1, or a pharmaceutically acceptable salt or counterion thereof, is 50 µg, 110 µg, 170 µg, 230 µg, 290 µg, 300 µg, 350 µg, 410 µg, 480 µg, 540 µg or 600 µg, 660 µg, 720 µg, 780 µg, 840 µg, or 900 µg. A preferred dose of the peptide of SEQ ID No. 1, or a pharmaceutically acceptable salt or counterion thereof, is 50 µg, 110 µg, 170 µg, 230 µg, 290 µg, 300 µg, 350 µg, 410 µg, 480 µg, 540 µg or 600 µg, 660 µg, 720 µg, 780 µg, 840 µg, or 900 µg per day. Another preferred dose of the peptide of SEQ ID No. 1, or a pharmaceutically acceptable salt or counterion thereof, is 300 µg. Another preferred dose of the peptide of SEQ ID No. 1, or a pharmaceutically acceptable salt or counterion thereof, is 300 µg per day.

The dose range of active ingredient (the peptide of SEQ ID No. 1, or a pharmaceutically acceptable salt or counterion thereof) administered to the patient is about 0.1 µg/kg to about 70 µg/kg of the patient's body weight, preferably the dose range is about 3 µg/kg to about 28 µg/kg of the patient's body weight; and more preferably the dose range is about 6 µg/kg to about 10 µg/kg of the patient's body weight. The dose may be a single one or a series of two or more given in the course of one or more days, as is needed by the patient. Further, the dose and perhaps dose frequency will also vary according to the age, body weight, and response of the individual patient.

In cases of administration of a pharmaceutically acceptable salt or counterion, dosages may be calculated as the free acid. In another embodiment of the present invention, the pharmaceutical composition is administered 1 to 4 times per day. In another embodiment, the pharmaceutical composition is administered 1 to 2 times per day. In another embodiment, the pharmaceutical composition is administered 1 time per day. In another embodiment, the pharmaceutical composition is administered for a period of continuous therapy, for example for a week or more, or for months or years.

The dosage strength of the peptide of SEQ ID No. 1, or a pharmaceutically acceptable salt or counterion thereof, for incorporation into the pharmaceutical compositions of the present invention is an amount from about 0.1 mg/mL to about 20 mg/mL of the active moiety in the constituted solution. In another embodiment, the dosage strength of the peptide of SEQ ID No. 1, or a pharmaceutically acceptable salt or counterion thereof, is an amount from about 0.5 mg/mL of the active moiety to about 10 mg/mL of the active moiety in the constituted solution. In another embodiment, the dosage strength of the peptide of SEQ ID No. 1, or a pharmaceutically acceptable salt or counterion thereof, is an amount from about 0.5 mg/mL to about 4 mg/mL of the active moiety in the constituted solution. In another embodiment, the dosage strength of the peptide of SEQ ID No. 1, or a pharmaceutically acceptable salt or counterion thereof, is 1 mg/mL of the active moiety in the constituted solution. In another embodiment, the dosage strength of the peptide of SEQ ID No. 1, or a pharmaceutically acceptable salt or counterion thereof, is 2 mg per mL of the active moiety in the constituted solution.

Specific embodiments of dosage strengths for the peptide of SEQ ID No. 1, or a pharmaceutically acceptable salt or counterion thereof, in the compositions of the present invention include, but are not limited to, the following:

(1) 33 milligrams of the peptide of SEQ ID No. 1, or a pharmaceutically acceptable salt or counterion thereof, in a cartridge or vial;
(2) 13.2 milligrams of the peptide of SEQ ID No. 1, or a pharmaceutically acceptable salt or counterion thereof, in a cartridge or vial;
(3) 6.6 milligrams of the peptide of SEQ ID No. 1, or a pharmaceutically acceptable salt or counterion thereof, in a cartridge or vial;
(4) 3.3 milligrams of the peptide of SEQ ID No. 1, or a pharmaceutically acceptable salt or counterion thereof, in a 3 milliliter cartridge or vial; and
(5) 0.33 milligrams of the peptide of SEQ ID No. 1, or a pharmaceutically acceptable salt or counterion thereof, in a cartridge or vial.

The solid pharmaceutical compositions may contain one or more bulking agents. Examples of bulking agents include, but are not limited to: sucrose, mannitol, glycine, lactose, trehalose, dextran, povidone, and sorbitol. In another embodiment of the present invention, the bulking agent is selected from: sucrose, mannitol, glycine, lactose, trehalose, dextran, povidone, and sorbitol. In another embodiment of the present invention, the bulking agent is selected from: trehalose, mannitol, and sucrose.

Acceptable additional bulking agents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety.

Preferred dosage forms for the pharmaceutical compositions of the present invention are vials, cartridges or ready to use syringes containing a solution of the pharmaceutical composition in water. A first vial, cartridge or syringe may contain the peptide of SEQ ID No. 1 and a second vial, cartridge or syringe may contain a solvent such as water; or a custom solvent including but not limited to a saline solution or a 5% dextrose solution; or a custom diluent including but not limited to the custom diluent disclosed in Example 2 and Example 3, for dissolving or constituting the pharmaceutical composition prior to injection. The solution may be administered by syringe or by any other suitable liquid injection device as a single dose per day or in multiple doses over a single or multiple day dosing regimen.

In another embodiment of the present invention, the pharmaceutical composition comprises
1) about 0.1 mg/mL-10 mg/mL of the peptide of SEQ ID NO. 1, or a pharmaceutically acceptable salt or counterion thereof; and
2) about 8 mg/mL-30 mg/mL of an anti-microbial agent, after constitution with a solvent, a custom solvent, or a custom diluent.

In a class of this embodiment, the pharmaceutical composition additionally comprises 1) about 0.1 mg/mL-15 mg/mL of a buffer; and/or 2) about 0.05 mg/mL-5 mg/mL of an anti-oxidant; and/or 3) about 10 mg/mL-60 mg/mL of a tonicity agent.

In another class of this embodiment, the pharmaceutical composition comprises
1) about 0.1 mg/mL-10 mg/mL of the peptide of SEQ ID NO. 1, or a pharmaceutically acceptable salt or counterion thereof;
2) about 8 mg/mL-30 mg/mL of an anti-microbial agent,
3) about 0.1 mg/mL-15 mg/mL of a buffer;
4) about 0.05 mg/mL-5 mg/mL of an anti-oxidant; and
5) about 10 mg/mL-60 mg/mL of a tonicity agent; after constitution with a solvent, or a custom solvent.

In another class of this embodiment, the anti-microbial agent is selected from: 1) phenol; 2) m-cresol; 3) benzyl alcohol; and 4) benzalkonium chloride; or a combination of two or more thereof. In another class of this embodiment, the anti-microbial agent is phenol and/or benzyl alcohol. In another class of this embodiment, the anti-microbial agent is m-cresol and/or benzyl alcohol. In another class of this embodiment, the anti-microbial agent is benzalkonium chloride and/or benzyl alcohol. In another class of this embodiment, the anti-microbial agent is phenol. In another class of this embodiment, the anti-microbial agent is m-cresol. In another class of this embodiment, the anti-microbial agent is benzalkonium chloride. In another class of this embodiment, the anti-microbial agent is benzyl alcohol.

In another class of this embodiment, the buffer is selected from: 1) sodium phosphate and dibasic sodium phosphate dihydrate; 2) tri(hydroxymethyl)aminomethane (TRIS or THAM), and 3) L-histidine, or a combination thereof. In another class of this embodiment, the buffer is sodium phosphate and dibasic sodium phosphate dihydrate. In another class of this embodiment, the buffer is tri(hydroxymethyl)aminomethane (TRIS or THAM). In another class of this embodiment, the buffer is L-histidine.

In another class of this embodiment, the tonicity agent is selected from: 1) propylene glycol; 2) mannitol; 3) glycerol;

and 4) sucrose, or a combination thereof. In another class of this embodiment, the tonicity agent is selected from: 1) propylene glycol, and 2) sucrose. In another class of this embodiment, the tonicity agent is propylene glycol. In another class of this embodiment, the tonicity agent is mannitol. In another class of this embodiment, the tonicity agent is glycerol. In another embodiment of the present invention, the tonicity agent is sucrose.

In another class of this embodiment, the anti-oxidant is selected from: 1) L-methionine; 2) ethylenediamine tetra acetic acid, or a salt and/or hydrate thereof; and 3) a combination of L-methionine and ethylenediamine tetra acetic acid, or a salt and/or hydrate thereof. In another class of this embodiment, the anti-oxidant is L-methionine. In another class of this embodiment, the anti-oxidant is selected from: ethylenediamine tetra acetic acid or a salt and/or hydrate thereof. In another embodiment of the present invention, the anti-oxidant is a combination of L-methionine and ethylenediamine tetra acetic acid, or a salt and/or hydrate thereof. In another embodiment of the present invention, the anti-oxidant is a combination of L-methionine and ethylenediamine tetra acetic acid (EDTA) disodium dihydrate.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In another class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

In another class of this embodiment, the custom diluent is the custom diluent of Example 2. In another class of this embodiment, the custom diluent is the custom diluent of Example 3. In a subclass of this class, the custom diluent is added to obtain a 1 mL solution of the pharmaceutical composition. In another subclass of this class, the custom diluent is added to obtain a 2 mL solution of the pharmaceutical composition. In another subclass of this class, the custom diluent is added to obtain a 3 mL solution of the pharmaceutical composition.

In another embodiment of the present invention, the pharmaceutical composition comprises
 1) about 0.1%-56% by weight of the peptide of SEQ ID NO. 1, or a pharmaceutically acceptable salt or counterion thereof; and
 2) about 9.6%-99.7% by weight of an anti-microbial agent; before constitution with a solvent, a custom solvent, or a custom diluent.

In another embodiment of the present invention, the pharmaceutical composition comprises
 1) about 0.1%-56% by weight of the peptide of SEQ ID NO. 1, or a pharmaceutically acceptable salt or counterion thereof;
 2) about 9.6%-99.7% by weight of an anti-microbial agent,
 3) about 0.1%-46% by weight of a buffer;
 4) about 0.1%-38% by weight of an anti-oxidant; and
 5) about 14%-88% by weight of a tonicity agent; before constitution with a solvent, or a custom solvent.

In a class of this embodiment, the pharmaceutical composition additionally comprises: 1) about 0.1%-46% by weight of a buffer; and/or 2) about 0.1%-38% by weight of an anti-oxidant; and/or 3) about 14%-88% by weight of a tonicity agent.

In another class of this embodiment, the anti-microbial agent is selected from: 1) phenol; 2) m-cresol; 3) benzyl alcohol; and 4) benzalkonium chloride; or a combination of two or more thereof. In another class of this embodiment, the anti-microbial agent is phenol and/or benzyl alcohol. In another class of this embodiment, the anti-microbial agent is m-cresol and/or benzyl alcohol. In another class of this embodiment, the anti-microbial agent is benzalkonium chloride and/or benzyl alcohol. In another class of this embodiment, the anti-microbial agent is phenol. In another class of this embodiment, the anti-microbial agent is m-cresol. In another class of this embodiment, the anti-microbial agent is benzalkonium chloride. In another class of this embodiment, the anti-microbial agent is benzyl alcohol.

In another class of this embodiment, the buffer is selected from: 1) sodium phosphate and dibasic sodium phosphate dihydrate; 2) tri(hydroxymethdyl)aminomethane (TRIS or THAM), and 3) L-histidine, or a combination thereof. In another class of this embodiment, the buffer is sodium phosphate and dibasic sodium phosphate dihydrate. In another class of this embodiment, the buffer is tri(hydroxymethdyl)aminomethane (TRIS or THAM). In another class of this embodiment, the buffer is L-histidine.

In another class of this embodiment, the tonicity agent is selected from: 1) propylene glycol; 2) mannitol; 3) glycerol; and 4) sucrose, or a combination thereof. In another class of this embodiment, the tonicity agent is selected from: 1) propylene glycol, and 2) sucrose. In another class of this embodiment, the tonicity agent is propylene glycol. In another class of this embodiment, the tonicity agent is mannitol. In another class of this embodiment, the tonicity agent is glycerol. In another embodiment of the present invention, the tonicity agent is sucrose.

In another class of this embodiment, the anti-oxidant is selected from: 1) L-methionine; 2) ethylenediamine tetra acetic acid, or a salt and/or hydrate thereof; and 3) a combination of L-methionine and ethylenediamine tetra acetic acid, or a salt and/or hydrate thereof. In another class of this embodiment, the anti-oxidant is L-methionine. In another class of this embodiment, the anti-oxidant is selected from: ethylenediamine tetra acetic acid or a salt and/or hydrate thereof. In another embodiment of the present invention, the anti-oxidant is a combination of L-methionine and ethylenediamine tetra acetic acid, or a salt and/or hydrate thereof. In another embodiment of the present invention, the anti-oxidant is a combination of L-methionine and ethylenediamine tetra acetic acid (EDTA) disodium dihydrate.

In another class of this embodiment, the pharmaceutical composition additionally comprises a solvent, a custom solvent, or a custom diluent.

In a subclass of this embodiment, the solvent is water. In a subclass of this subclass, water is added to obtain a 1 mL solution of the pharmaceutical composition. In another subclass of this subclass, water is added to obtain a 2 mL solution of the pharmaceutical composition. In another subclass of this subclass, water is added to obtain a 3 mL solution of the pharmaceutical composition.

In another subclass of this class, the pH of the composition in water is about pH 6.7 to about pH 8.4. In another subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another subclass of this class, the custom solvent is a saline solution in water. In another subclass of this class, the custom solvent is a 5% dextrose solution in water. In a subclass of this subclass, the custom solvent is added to obtain a 1 mL solution of the pharmaceutical composition. In another subclass of this subclass, the custom solvent is added to obtain a 2 mL solution of the pharmaceutical composition. In another subclass of this subclass, the custom solvent is added to obtain a 3 mL solution of the pharmaceutical composition.

In another subclass of this class, the custom diluent is the custom diluent of Example 2. In another subclass of this class, the custom diluent is the custom diluent of Example 3. In a subclass of this subclass, the custom diluent is added to obtain a 1 mL solution of the pharmaceutical composition. In another subclass of this subclass, the custom diluent is added to obtain a 2 mL solution of the pharmaceutical composition. In another subclass of this subclass, the custom diluent is added to obtain a 3 mL solution of the pharmaceutical composition.

In another embodiment of the present invention, the pharmaceutical composition comprises
1) about 0.01%-1% by weight of the peptide of SEQ ID NO. 1, or a pharmaceutically acceptable salt or counterion thereof; and
2) about 0.8% -3% by weight of an anti-microbial agent, after constitution with a solvent, a custom solvent, or a custom diluent.

In a class of this embodiment, the pharmaceutical composition additionally comprises 1) about 0.01%-1.5% by weight of a buffer; and/or 2) about 0.05%-0.5% by weight of an anti-oxidant; and/or 3) about 1%-6% by weight of a tonicity agent.

In another class of this embodiment, the pharmaceutical composition comprises
1) about 0.01%-1% by weight of the peptide of SEQ ID NO. 1, or a pharmaceutically acceptable salt or counterion thereof;
2) about 0.8% -3% by weight of an anti-microbial agent;
3) about 0.01%-1.5% by weight of a buffer;
4) about 0.05%-0.5% by weight of an anti-oxidant; and
5) about 1%-6% by weight of a tonicity agent; after constitution with a solvent, or a custom solvent.

In another class of this embodiment, the anti-microbial agent is selected from: 1) phenol; 2) m-cresol; 3) benzyl alcohol; and 4) benzalkonium chloride; or a combination of two or more thereof. In another class of this embodiment, the anti-microbial agent is phenol and/or benzyl alcohol. In another class of this embodiment, the anti-microbial agent is m-cresol and/or benzyl alcohol. In another class of this embodiment, the anti-microbial agent is benzalkonium chloride and/or benzyl alcohol. In another class of this embodiment, the anti-microbial agent is phenol. In another class of this embodiment, the anti-microbial agent is m-cresol. In another class of this embodiment, the anti-microbial agent is benzalkonium chloride. In another class of this embodiment, the anti-microbial agent is benzyl alcohol.

In another class of this embodiment, the buffer is selected from: 1) sodium phosphate and dibasic sodium phosphate dihydrate; 2) tri(hydroxymethdyl)aminomethane (TRIS or THAM), and 3) L-histidine, or a combination thereof. In another class of this embodiment, the buffer is sodium phosphate and dibasic sodium phosphate dihydrate. In another class of this embodiment, the buffer is tri(hydroxymethdyl)aminomethane (TRIS or THAM). In another class of this embodiment, the buffer is L-histidine.

In another class of this embodiment, the tonicity agent is selected from: 1) propylene glycol; 2) mannitol; 3) glycerol; and 4) sucrose, or a combination thereof. In another class of this embodiment, the tonicity agent is selected from: 1) propylene glycol, and 2) sucrose. In another class of this embodiment, the tonicity agent is propylene glycol. In another class of this embodiment, the tonicity agent is mannitol. In another class of this embodiment, the tonicity agent is glycerol. In another embodiment of the present invention, the tonicity agent is sucrose.

In another class of this embodiment, the anti-oxidant is selected from: 1) L-methionine; 2) ethylenediamine tetra acetic acid, or a salt and/or hydrate thereof; and 3) a combination of L-methionine and ethylenediamine tetra acetic acid, or a salt and/or hydrate thereof. In another class of this embodiment, the anti-oxidant is L-methionine. In another class of this embodiment, the anti-oxidant is selected from: ethylenediamine tetra acetic acid or a salt and/or hydrate thereof. In another embodiment of the present invention, the anti-oxidant is a combination of L-methionine and ethylenediamine tetra acetic acid, or a salt and/or hydrate thereof. In another embodiment of the present invention, the anti-oxidant is a combination of L-methionine and ethylenediamine tetra acetic acid (EDTA) disodium dihydrate.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In another class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

In another class of this embodiment, the custom diluent is the custom diluent of Example 2. In another class of this embodiment, the custom diluent is the custom diluent of Example 3. In a subclass of this class, the custom diluent is added to obtain a 1 mL solution of the pharmaceutical composition. In another subclass of this class, the custom diluent is added to obtain a 2 mL solution of the pharmaceutical composition. In another subclass of this class, the custom diluent is added to obtain a 3 mL solution of the pharmaceutical composition.

In another embodiment of the present invention, the pharmaceutical composition comprises:
1) about 0.5 mg/mL-4 mg/mL of the peptide of SEQ ID No. 1, or a pharmaceutically acceptable salt or counterion thereof;
2) about 13 mg/mL-25 mg/mL of an anti-microbial agent;
3) about 1 mg/mL-10 mg/mL of a buffer;
4) about 0.1 mg/mL-3.5 mg/mL of an anti-oxidant; and
5) about 20 mg/mL-50 mg/mL of a tonicity agent,
after constitution with a solvent, or a custom solvent.

In a class of this embodiment, the anti-microbial agent is selected from: 1) phenol; 2) m-cresol; 3) benzyl alcohol; and 4) benzalkonium chloride; or a combination of two or more thereof. In another class of this embodiment, the anti-microbial agent is phenol and/or benzyl alcohol. In another class of this embodiment, the anti-microbial agent is m-cresol and/or benzyl alcohol. In another class of this embodiment, the anti-microbial agent is benzalkonium chloride and/or benzyl alcohol. In another class of this embodiment, the anti-microbial agent is phenol. In another class of this embodiment, the anti-microbial agent is m-cresol. In another class of this embodiment, the anti-microbial agent is benzalkonium chloride. In another class of this embodiment, the anti-microbial agent is benzyl alcohol.

In another class of this embodiment, the buffer is selected from: 1) sodium phosphate and dibasic sodium phosphate dihydrate; 2) tri(hydroxymethdyl)aminomethane (TRIS or THAM), and 3) L-histidine, or a combination thereof. In another class of this embodiment, the buffer is sodium phosphate and dibasic sodium phosphate dihydrate. In another class of this embodiment, the buffer is tri(hydroxymethdyl)aminomethane (TRIS or THAM). In another class of this embodiment, the buffer is L-histidine.

In another class of this embodiment, the tonicity agent is selected from: 1) propylene glycol; 2) mannitol; 3) glycerol; and 4) sucrose, or a combination thereof. In another class of this embodiment, the tonicity agent is selected from: 1) propylene glycol, and 2) sucrose. In another class of this embodiment, the tonicity agent is propylene glycol. In another class of this embodiment, the tonicity agent is mannitol. In another class of this embodiment, the tonicity agent is glycerol. In another embodiment of the present invention, the tonicity agent is sucrose.

In another class of this embodiment, the anti-oxidant is selected from: 1) L-methionine; 2) ethylenediamine tetra acetic acid, or a salt and/or hydrate thereof; and 3) a combination of L-methionine and ethylenediamine tetra acetic acid, or a salt and/or hydrate thereof. In another class of this embodiment, the anti-oxidant is L-methionine. In another class of this embodiment, the anti-oxidant is selected from: ethylenediamine tetra acetic acid or a salt and/or hydrate thereof. In another embodiment of the present invention, the anti-oxidant is a combination of L-methionine and ethylenediamine tetra acetic acid, or a salt and/or hydrate thereof. In another embodiment of the present invention, the anti-oxidant is a combination of L-methionine and ethylenediamine tetra acetic acid (EDTA) disodium dihydrate.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In another class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

In another embodiment of the present invention, the pharmaceutical composition comprises:
1) about 0.6%-24% by weight of the peptide of SEQ ID No. 1, or a pharmaceutically acceptable salt or counterion thereof;
2) about 10.2%-98.8 by weight of an anti-microbial agent;
3) about 1.2%-43% by weight of a buffer;
4) about 0.1% -21% by weight of an anti-oxidant; and
5) about 34%-79% by weight of a tonicity agent,
before constitution with a solvent, or a custom solvent.

In a class of this embodiment, the anti-microbial agent is selected from: 1) phenol; 2) m-cresol; 3) benzyl alcohol; and 4) benzalkonium chloride; or a combination of two or more thereof. In another class of this embodiment, the anti-microbial agent is phenol and/or benzyl alcohol. In another class of this embodiment, the anti-microbial agent is m-cresol and/or benzyl alcohol. In another class of this embodiment, the anti-microbial agent is benzalkonium chloride and/or benzyl alcohol. In another class of this embodiment, the anti-microbial agent is phenol. In another class of this embodiment, the anti-microbial agent is m-cresol. In another class of this embodiment, the anti-microbial agent is benzalkonium chloride. In another class of this embodiment, the anti-microbial agent is benzyl alcohol.

In another class of this embodiment, the buffer is selected from: 1) sodium phosphate and dibasic sodium phosphate dihydrate; 2) tri(hydroxymethdyl)aminomethane (TRIS or THAM), and 3) L-histidine, or a combination thereof. In another class of this embodiment, the buffer is sodium phosphate and dibasic sodium phosphate dihydrate. In another class of this embodiment, the buffer is tri(hydroxymethdyl)aminomethane (TRIS or THAM). In another class of this embodiment, the buffer is L-histidine.

In another class of this embodiment, the tonicity agent is selected from: 1) propylene glycol; 2) mannitol; 3) glycerol; and 4) sucrose, or a combination thereof. In another class of this embodiment, the tonicity agent is selected from: 1) propylene glycol, and 2) sucrose. In another class of this embodiment, the tonicity agent is propylene glycol. In another class of this embodiment, the tonicity agent is mannitol. In another class of this embodiment, the tonicity agent is glycerol. In another embodiment of the present invention, the tonicity agent is sucrose.

In another class of this embodiment, the anti-oxidant is selected from: 1) L-methionine; 2) ethylenediamine tetra acetic acid, or a salt and/or hydrate thereof; and 3) a combination of L-methionine and ethylenediamine tetra acetic acid, or a salt and/or hydrate thereof. In another class of this embodiment, the anti-oxidant is L-methionine. In another class of this embodiment, the anti-oxidant is selected from: ethylenediamine tetra acetic acid or a salt and/or hydrate thereof. In another embodiment of the present invention, the anti-oxidant is a combination of L-methionine and ethylenediamine tetra acetic acid, or a salt and/or hydrate thereof. In another embodiment of the present invention, the anti-oxidant is a combination of L-methionine and ethylenediamine tetra acetic acid (EDTA) disodium dihydrate.

In another class of this embodiment, the pharmaceutical composition additionally comprises a solvent, or a custom solvent.

In a subclass of this class, the solvent is water. In another subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In another subclass of this class, the pH of the composition in water is about pH 6.7 to about pH 8.4. In another subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another subclass of this class, the custom solvent is a saline solution in water. In another subclass of this class, the custom solvent is a 5% dextrose solution in water. In a subclass of this subclass, the custom solvent is added to obtain a 1 mL solution of the pharmaceutical composition. In another subclass of this subclass, the custom solvent is added to obtain a 2 mL solution of the pharmaceutical composition. In another subclass of this subclass, the custom solvent is added to obtain a 3 mL solution of the pharmaceutical composition.

In another embodiment of the present invention, the pharmaceutical composition comprises:
1) about 0.05%-0.4% by weight of the peptide of SEQ ID No. 1, or a pharmaceutically acceptable salt or counterion thereof;
2) about 1.3%-2.5% by weight of an anti-microbial agent;
3) about 0.1%-10.9% by weight of a buffer;
4) about 0.15%-0.3% by weight of an anti-oxidant; and
5) about 2%-5% by weight of a tonicity agent,
after constitution with a solvent, or a custom solvent.

In a class of this embodiment, the anti-microbial agent is selected from: 1) phenol; 2) m-cresol; 3) benzyl alcohol; and 4) benzalkonium chloride; or a combination of two or more thereof. In another class of this embodiment, the anti-microbial agent is phenol and/or benzyl alcohol. In another class of this embodiment, the anti-microbial agent is m-cresol and/or benzyl alcohol. In another class of this embodiment, the anti-microbial agent is benzalkonium chloride and/or benzyl alcohol. In another class of this embodiment, the anti-microbial agent is phenol. In another class of this embodiment, the anti-microbial agent is m-cresol. In another class of this embodiment, the anti-microbial agent is benzalkonium chloride. In another class of this embodiment, the anti-microbial agent is benzyl alcohol.

In another class of this embodiment, the buffer is selected from: 1) sodium phosphate and dibasic sodium phosphate dihydrate; 2) tri(hydroxymethdyl)aminomethane (TRIS or THAM), and 3) L-histidine, or a combination thereof. In another class of this embodiment, the buffer is sodium phosphate and dibasic sodium phosphate dihydrate. In another class of this embodiment, the buffer is tri(hydroxymethdyl)aminomethane (TRIS or THAM). In another class of this embodiment, the buffer is L-histidine.

In another class of this embodiment, the tonicity agent is selected from: 1) propylene glycol; 2) mannitol; 3) glycerol; and 4) sucrose, or a combination thereof. In another class of this embodiment, the tonicity agent is selected from: 1) propylene glycol, and 2) sucrose. In another class of this embodiment, the tonicity agent is propylene glycol. In another class of this embodiment, the tonicity agent is mannitol. In another class of this embodiment, the tonicity agent is glycerol. In another embodiment of the present invention, the tonicity agent is sucrose.

In another class of this embodiment, the anti-oxidant is selected from: 1) L-methionine; 2) ethylenediamine tetra acetic acid, or a salt and/or hydrate thereof; and 3) a combination of L-methionine and ethylenediamine tetra acetic acid, or a salt and/or hydrate thereof. In another class of this embodiment, the anti-oxidant is L-methionine. In another class of this embodiment, the anti-oxidant is selected from: ethylenediamine tetra acetic acid or a salt and/or hydrate thereof. In another embodiment of the present invention, the anti-oxidant is a combination of L-methionine and ethylenediamine tetra acetic acid, or a salt and/or hydrate thereof. In another embodiment of the present invention, the anti-oxidant is a combination of L-methionine and ethylenediamine tetra acetic acid (EDTA) disodium dihydrate.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In another class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

In another embodiment of the present invention, the pharmaceutical composition comprises:
1) about 1 mg/mL-3 mg/mL of the peptide of SEQ ID No. 1, or a pharmaceutically acceptable salt or counterion thereof;
2) about 15 mg/mL-23 mg/mL of an anti-microbial agent;
3) about 4 mg/mL-9 mg/mL of a buffer;
4) about 1 mg/mL-2 mg/mL of an anti-oxidant; and
5) about 20 mg/mL-40 mg/mL of a tonicity agent,
after constitution with a solvent, or a custom solvent.

In a class of this embodiment, the anti-microbial agent is selected from: 1) phenol; 2) m-cresol; 3) benzyl alcohol; and 4) benzalkonium chloride; or a combination of two or more thereof. In another class of this embodiment, the anti-microbial agent is phenol and/or benzyl alcohol. In another class of this embodiment, the anti-microbial agent is m-cresol and/or benzyl alcohol. In another class of this embodiment, the anti-microbial agent is benzalkonium chloride and/or benzyl alcohol. In another class of this embodiment, the anti-microbial agent is phenol. In another class of this embodiment, the anti-microbial agent is m-cresol. In another class of this embodiment, the anti-microbial agent is benzalkonium chloride. In another class of this embodiment, the anti-microbial agent is benzyl alcohol.

In another class of this embodiment, the buffer is selected from: 1) sodium phosphate and dibasic sodium phosphate dihydrate; 2) tri(hydroxymethdyl)aminomethane (TRIS or THAM), and 3) L-histidine, or a combination thereof. In another class of this embodiment, the buffer is sodium phosphate and dibasic sodium phosphate dihydrate. In another class of this embodiment, the buffer is tri(hydroxymethdyl)aminomethane (TRIS or THAM). In another class of this embodiment, the buffer is L-histidine.

In another class of this embodiment, the tonicity agent is selected from: 1) propylene glycol; 2) mannitol; 3) glycerol; and 4) sucrose, or a combination thereof. In another class of this embodiment, the tonicity agent is selected from: 1) propylene glycol, and 2) sucrose. In another class of this embodiment, the tonicity agent is propylene glycol. In another class of this embodiment, the tonicity agent is mannitol. In another class of this embodiment, the tonicity agent is glycerol. In another embodiment of the present invention, the tonicity agent is sucrose.

In another class of this embodiment, the anti-oxidant is selected from: 1) L-methionine; 2) ethylenediamine tetra acetic acid, or a salt and/or hydrate thereof; and 3) a combination of L-methionine and ethylenediamine tetra acetic acid, or a salt and/or hydrate thereof. In another class of this embodiment, the anti-oxidant is L-methionine. In another class of this embodiment, the anti-oxidant is selected from: ethylenediamine tetra acetic acid or a salt and/or hydrate thereof. In another embodiment of the present invention, the anti-oxidant is a combination of L-methionine and ethylenediamine tetra acetic acid, or a salt and/or hydrate thereof. In another embodiment of the present invention, the anti-oxidant is a combination of L-methionine and ethylenediamine tetra acetic acid (EDTA) disodium dihydrate.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In a class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

In another embodiment of the present invention, the pharmaceutical composition comprises:
1) about 1.3%-17% by weight of the peptide of SEQ ID No. 1, or a pharmaceutically acceptable salt or counterion thereof;
2) about 22%-94% by weight of an anti-microbial agent;
3) about 5.6%-36% by weight of a buffer;
4) about 1.5-11% by weight of an anti-oxidant; and
5) about 42%-72% by weight of a tonicity agent,
before constitution with a solvent, or a custom solvent.

In a class of this embodiment, the anti-microbial agent is selected from: 1) phenol; 2) m-cresol; 3) benzyl alcohol; and 4) benzalkonium chloride; or a combination of two or more thereof. In another class of this embodiment, the anti-microbial agent is phenol and/or benzyl alcohol. In another class of this embodiment, the anti-microbial agent is m-cresol and/or benzyl alcohol. In another class of this embodiment, the anti-microbial agent is benzalkonium chloride and/or benzyl alcohol. In another class of this embodiment, the anti-microbial agent is phenol. In another class of this embodiment, the anti-microbial agent is m-cresol. In another class of this embodiment, the anti-microbial agent is benzalkonium chloride. In another class of this embodiment, the anti-microbial agent is benzyl alcohol.

In another class of this embodiment, the buffer is selected from: 1) sodium phosphate and dibasic sodium phosphate dihydrate; 2) tri(hydroxymethdyl)aminomethane (TRIS or THAM), and 3) L-histidine, or a combination thereof. In another class of this embodiment, the buffer is sodium phosphate and dibasic sodium phosphate dihydrate. In another class of this embodiment, the buffer is tri(hydroxymethdyl)aminomethane (TRIS or THAM). In another class of this embodiment, the buffer is L-histidine.

In another class of this embodiment, the tonicity agent is selected from: 1) propylene glycol; 2) mannitol; 3) glycerol; and 4) sucrose, or a combination thereof. In another class of this embodiment, the tonicity agent is selected from: 1) propylene glycol, and 2) sucrose. In another class of this embodiment, the tonicity agent is propylene glycol. In another class of this embodiment, the tonicity agent is mannitol. In another class of this embodiment, the tonicity agent is glycerol. In another embodiment of the present invention, the tonicity agent is sucrose.

In another class of this embodiment, the anti-oxidant is selected from: 1) L-methionine;
2) ethylenediamine tetra acetic acid, or a salt and/or hydrate thereof; and 3) a combination of L-methionine and ethylenediamine tetra acetic acid, or a salt and/or hydrate thereof. In another class of this embodiment, the anti-oxidant is L-methionine. In another class of this embodiment, the anti-oxidant is selected from: ethylenediamine tetra acetic acid or a salt and/or hydrate thereof. In another embodiment of the present invention, the anti-oxidant is a combination of L-methionine and ethylenediamine tetra acetic acid, or a salt and/or hydrate thereof. In another embodiment of the present invention, the anti-oxidant is a combination of L-methionine and ethylenediamine tetra acetic acid (EDTA) disodium dihydrate.

In another class of this embodiment, the pharmaceutical composition additionally comprises a solvent, or a custom solvent.

In a subclass of this class, the solvent is water. In a subclass of this subclass, water is added to obtain a 1 mL solution of the pharmaceutical composition. In another subclass of this subclass, water is added to obtain a 2 mL solution of the pharmaceutical composition. In another subclass of this subclass, water is added to obtain a 3 mL solution of the pharmaceutical composition.

In another subclass of this class, the pH of the composition in water is about pH 6.7 to about pH 8.4. In another subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another subclass of this class, the custom solvent is a saline solution in water. In another subclass of this class, the custom solvent is a 5% dextrose solution in water. In a subclass of this subclass, the custom solvent is added to obtain a 1 mL solution of the pharmaceutical composition. In another subclass of this subclass, the custom solvent is added to obtain a 2 mL solution of the pharmaceutical composition. In another subclass of this subclass, the custom solvent is added to obtain a 3 mL solution of the pharmaceutical composition.

In another embodiment of the present invention, the pharmaceutical composition comprises:
1) about 0.1%-0.3% by weight of the peptide of SEQ ID No. 1, or a pharmaceutically acceptable salt or counterion thereof;
2) about 1.5%-2.3% by weight of an anti-microbial agent;
3) about 0.4%-0.9% by weight of a buffer;
4) about 0.1%-0.2% by weight of an anti-oxidant; and
5) about 2%-3% by weight of a tonicity agent,
after constitution with a solvent, or a custom solvent.

In a class of this embodiment, the anti-microbial agent is selected from: 1) phenol; 2) m-cresol; 3) benzyl alcohol; and 4) benzalkonium chloride; or a combination of two or more thereof. In another class of this embodiment, the anti-microbial agent is phenol and/or benzyl alcohol. In another class of this embodiment, the anti-microbial agent is m-cresol and/or benzyl alcohol. In another class of this embodiment, the anti-microbial agent is benzalkonium chloride and/or benzyl alcohol. In another class of this embodiment, the anti-microbial agent is phenol. In another class of this embodiment, the anti-microbial agent is m-cresol. In another class of this embodiment, the anti-microbial agent is benzalkonium chloride. In another class of this embodiment, the anti-microbial agent is benzyl alcohol.

In another class of this embodiment, the buffer is selected from: 1) sodium phosphate and dibasic sodium phosphate dihydrate; 2) tri(hydroxymethdyl)aminomethane (TRIS or THAM), and 3) L-histidine, or a combination thereof. In another class of this embodiment, the buffer is sodium phosphate and dibasic sodium phosphate dihydrate. In another class of this embodiment, the buffer is tri(hydroxymethdyl)aminomethane (TRIS or THAM). In another class of this embodiment, the buffer is L-histidine.

In another class of this embodiment, the tonicity agent is selected from: 1) propylene glycol; 2) mannitol; 3) glycerol; and 4) sucrose, or a combination thereof. In another class of this embodiment, the tonicity agent is selected from: 1) propylene glycol, and 2) sucrose. In another class of this embodiment, the tonicity agent is propylene glycol. In another class of this embodiment, the tonicity agent is mannitol. In another class of this embodiment, the tonicity agent is glycerol. In another embodiment of the present invention, the tonicity agent is sucrose.

In another class of this embodiment, the anti-oxidant is selected from: 1) L-methionine; 2) ethylenediamine tetra acetic acid, or a salt and/or hydrate thereof; and 3) a combination of L-methionine and ethylenediamine tetra acetic acid, or a salt and/or hydrate thereof. In another class of this embodiment, the anti-oxidant is L-methionine. In another class of this embodiment, the anti-oxidant is selected from: ethylenediamine tetra acetic acid or a salt and/or hydrate thereof. In another embodiment of the present invention, the anti-oxidant is a combination of L-methionine and ethylenediamine tetra acetic acid, or a salt and/or hydrate thereof. In another embodiment of the present invention, the anti-oxidant is a combination of L-methionine and ethylenediamine tetra acetic acid (EDTA) disodium dihydrate.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition. In another class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

In another embodiment of the present invention, the pharmaceutical composition comprises:
1) about 1 mg/mL-3 mg/mL of the peptide of SEQ ID No. 1, or a pharmaceutically acceptable salt or counterion thereof;
2) about 15 mg/mL-20 mg/mL of benzyl alcohol;
3) about 6 mg/mL-9 mg/mL of L-histidine;
4) about 20 mg/mL-40 mg/mL of sucrose; and
5) about 1 mg/mL-2 mg/mL of L-methionine;

after constitution with a solvent, or a custom solvent.

In a class of this embodiment, the pharmaceutical composition comprises:
1) about 1 mg/mL-3 mg/mL of the peptide of SEQ ID No. 1, or a pharmaceutically acceptable salt or counterion thereof;
2) about 15 mg/mL-20 mg/mL of benzyl alcohol;
3) about 6 mg/mL-9 mg/mL of L-histidine;
4) about 20 mg/mL-40 mg/mL of sucrose;
5) about 1 mg/mL-2 mg/mL of L-methionine; and
6) about 0.1 mg/mL-0.7 mg/mL mg/mL by weight of ethylenediamine tetra acetic acid, or a salt and/or hydrate thereof, after constitution with a solvent or a custom solvent.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In another class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

In another embodiment of the present invention, the pharmaceutical composition comprises:
1) about 2%-4% by weight of the peptide of SEQ ID No. 1, or a pharmaceutically acceptable salt or counterion thereof;
2) about 28%-32% by weight of benzyl alcohol;
3) about 12%-14% by weight of L-histidine;
4) about 48%-52% by weight of sucrose; and
5) about 2%-3% by weight of L-methionine;

before constitution with a solvent, or a custom solvent.

In a class of this embodiment, the pharmaceutical composition comprises a solvent, or a custom solvent.

In another class of this embodiment the pharmaceutical composition comprises:
1) about 2%-4% by weight of the peptide of SEQ ID No. 1, or a pharmaceutically acceptable salt or counterion thereof;
2) about 28%-32% by weight of benzyl alcohol;
3) about 12%-14% by weight of L-histidine;
4) about 48%-52% by weight of sucrose;
5) about 2%-3% by weight of L-methionine; and
6) about 0.01%-0.5% by weight of ethylenediamine tetra acetic acid, or a salt and/or hydrate thereof, before constitution with a solvent, or a custom solvent.

In another class of this embodiment, the pharmaceutical composition additionally comprises a solvent, or a custom solvent.

In a subclass of this class, the solvent is water. In a subclass of this subclass, water is added to obtain a 1 mL solution of the pharmaceutical composition. In another subclass of this subclass, water is added to obtain a 2 mL solution of the pharmaceutical composition. In another subclass of this subclass, water is added to obtain a 3 mL solution of the pharmaceutical composition.

In another subclass of this class, the pH of the composition in water is about pH 6.7 to about pH 8.4. In another subclass of this subclass, the pH of the composition in water is about pH 6.8 to about pH 7.6. In another subclass of this subclass, the pH of the composition in water is about pH 6.9 to about pH 7.3. In another subclass of this subclass, the pH of the composition in water is about pH 7.1. In another subclass of this subclass, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1N hydrochloric acid.

In another subclass of this class, the custom solvent is a saline solution in water. In another subclass of this class, the custom solvent is a 5% dextrose solution in water. In a subclass of this subclass, the custom solvent is added to obtain a 1 mL solution of the pharmaceutical composition. In another subclass of this subclass, the custom solvent is added to obtain a 2 mL solution of the pharmaceutical composition. In another subclass of this subclass, the custom solvent is added to obtain a 3 mL solution of the pharmaceutical composition.

In another embodiment of the present invention, the pharmaceutical composition comprises:
1) about 0.01%-2% by weight of the peptide of SEQ ID No. 1, or a pharmaceutically acceptable salt or counterion thereof;
2) about 1%-3% by weight of benzyl alcohol;
3) about 0.5%-1% by weight of L-histidine;
4) about 2%-4% by weight of sucrose; and
5) about 0.01%-0.3% by weight of L-methionine;
after constitution with a solvent, or a custom solvent.

In a class of this embodiment, the pharmaceutical composition comprises:
1) about 0.01%-2% by weight of the peptide of SEQ ID No. 1, or a pharmaceutically acceptable salt or counterion thereof;
2) about 1%-3% by weight of benzyl alcohol;
3) about 0.5%-1% by weight of L-histidine;
4) about 2%-4% by weight of sucrose;
5) about 0.01%-0.3% by weight of L-methionine; and
6) about 0.01%-0.3% by weight of ethylenediamine tetra acetic acid, or a salt and/or hydrate thereof,
after constitution with a solvent, or a custom solvent.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In another class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

In another embodiment of the present invention, the pharmaceutical composition comprises:
1) about 2 mg/mL of the peptide of SEQ ID No. 1, or a pharmaceutically acceptable salt or counterion thereof;
2) about 18 mg/mL of benzyl alcohol;
3) about 7.75 mg/mL of L-histidine;
4) about 50 mg/mL of sucrose; and
5) about 1.49 mg/mL of L-methionine;
after constitution with a solvent, or a custom solvent In a class of this embodiment, the pharmaceutical composition comprises:
1) about 2 mg/mL of the peptide of SEQ ID No. 1, or a pharmaceutically acceptable salt or counterion thereof;
2) about 18 mg/mL of benzyl alcohol;
3) about 7.75 mg/mL of L-histidine;
4) about 50 mg/mL of sucrose;
5) about 1.49 mg/mL of L-methionine; and
6) about 0.37 mg/mL by weight of ethylenediamine tetra acetic acid disodium dihydrate;
after constitution with a solvent, or a custom solvent.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In another class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

In another embodiment of the present invention, the pharmaceutical composition comprises:
1) about 3% by weight of the peptide of SEQ ID No. 1, or a pharmaceutically acceptable salt or counterion thereof;
2) about 30% by weight of benzyl alcohol;
3) about 13% by weight of L-histidine;
4) about 51% by weight of sucrose; and
5) about 3% by weight of L-methionine;
before constitution with a solvent, or a custom solvent.

In a class of this embodiment, the pharmaceutical composition comprises:
1) about 3% by weight of the peptide of SEQ ID No. 1, or a pharmaceutically acceptable salt or counterion thereof;
2) about 30% by weight of benzyl alcohol;
3) about 13% by weight of L-histidine;
4) about 51% by weight of sucrose;
5) about 3% by weight of L-methionine; and
6) about 0.6% by weight of ethylenediamine tetra acetic acid disodium dihydrate, before constitution with a solvent, or a custom solvent.

In another class of this embodiment, the pharmaceutical composition additionally comprises a solvent, or a custom solvent.

In a subclass of this class, the solvent is water. In a subclass of this subclass, water is added to obtain a 1 mL solution of the pharmaceutical composition. In another subclass of this subclass, water is added to obtain a 2 mL solution of the pharmaceutical composition. In another subclass of this subclass, water is added to obtain a 3 mL solution of the pharmaceutical composition.

In another subclass of this class, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another subclass of this class, the custom solvent is a saline solution in water. In another subclass of this class, the custom solvent is a 5% dextrose solution in water. In a subclass of this subclass, the custom solvent is added to obtain a 1 mL solution of the pharmaceutical composition. In another subclass of this subclass, the custom solvent is added to obtain a 2 mL solution of the pharmaceutical composition. In another subclass of this subclass, the custom solvent is added to obtain a 3 mL solution of the pharmaceutical composition.

In another embodiment of the present invention, the pharmaceutical composition comprises:
1) about 0.2% by weight of the peptide of SEQ ID No. 1, or a pharmaceutically acceptable salt or counterion thereof;
2) about 1.8% by weight of benzyl alcohol;
3) about 0.78% by weight of L-histidine;
4) about 3% by weight of sucrose; and
5) about 0.15% by weight of L-methionine;
after constitution with a solvent, or a custom solvent.

In a class of this embodiment, the pharmaceutical composition comprises:
1) about 0.2% by weight of the peptide of SEQ ID No. 1, or a pharmaceutically acceptable salt or counterion thereof;
2) about 1.8% by weight of benzyl alcohol;
3) about 0.78% by weight of L-histidine;
4) about 3% by weight of sucrose;
5) about 0.15% by weight of L-methionine;
6) about 0.037% by weight of ethylenediamine tetra acetic acid disodium dihydrate, after constitution with a solvent, or a custom solvent.

In another class of this embodiment, the solvent is water. In a subclass of this class, water is added to obtain a 1 mL solution of the pharmaceutical composition. In another subclass of this class, water is added to obtain a 2 mL solution of the pharmaceutical composition. In another subclass of this class, water is added to obtain a 3 mL solution of the pharmaceutical composition.

In another class of this embodiment, the pH of the composition in water is about pH 6.7 to about pH 8.4. In a subclass of this class, the pH of the composition in water is about pH 6.8 to about pH 7.6. In another subclass of this class, the pH of the composition in water is about pH 6.9 to about pH 7.3. In another subclass of this class, the pH of the composition in water is about pH 7.1. In another subclass of this class, the pH of the composition in water is adjusted by the addition of a base and an acid. In a subclass of this subclass, the base is sodium hydroxide. In another subclass of this subclass, the base is 1 N sodium hydroxide. In another subclass of this subclass, the acid is hydrochloric acid. In another subclass of this subclass, the acid is 1 N hydrochloric acid.

In another class of this embodiment, the custom solvent is a saline solution in water. In another class of this embodiment, the custom solvent is a 5% dextrose solution in water. In a subclass of this class, the custom solvent is added to obtain a 1 mL solution of the pharmaceutical composition. In another subclass of this class, the custom solvent is added to obtain a 2 mL solution of the pharmaceutical composition. In another subclass of this class, the custom solvent is added to obtain a 3 mL solution of the pharmaceutical composition.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass compositions made by admixing the active ingredient(s), and pharmaceutically acceptable excipients.

There are a wide variety of excipients known in the pharmaceutical formulation art. According to the desired properties of the pharmaceutical composition, any number of ingredients may be selected, alone or in combination, based upon their known uses in preparing pharmaceutical compositions, such ingredients include, but are not limited to, binders, disintegrants, lubricants, surfactants, diluents, anti-oxidants, compression aids, glidants, flavors, flavor enhancers, sweeteners, and preservatives, and combinations thereof.

The term "weight percent" or "weight %" as used herein means the dry weight of each ingredient as a % of the total dry weight. This is the weight prior to constitution with water. The quantity of each excipient is expressed as a weight percentage of the pharmaceutical composition. Each of the weight percentage amounts noted for each excipient may be combined with any weight percentage amount noted for one or more of the other excipients, and all such combinations are encompassed within the scope of this invention.

The term "solvent" as used herein is a solvent such as water. In one embodiment the solvent is water.

The term "custom solvent" as used herein includes but is not limited to a saline solution, or a 5% dextrose solution in water. In one embodiment the custom solvent is a saline solution in water. In another embodiment, the custom solvent is a 5% dextrose solution in water.

The term "custom diluent" as used herein means a solvent or custom solvent and excipients. The term "custom diluent" as used herein includes but is not limited to the custom diluents in Examples 2 and 3. In one embodiment the custom diluent is the custom diluent of Example 2. In another embodiment, the custom diluent is the custom diluent of Example 3.

The pharmaceutical compositions described herein may be administered to a human patient per se, or in pharmaceutical compositions where the active ingredient is mixed with other active ingredients, as in combination therapy, or suitable carriers or excipient(s). The dosage form may comprise a sufficient amount of the peptide of SEQ ID No.

1, or a pharmaceutically acceptable salt or counterion thereof, to treat diabetes, or a diabetes-related disorder, as part of a particular administration protocol, as would be understood by those of skill in the art. Techniques for formulation and administration of compounds may be found in "Remington's Pharmaceutical Sciences," Mack Publishing Co., Easton, Pa., 18th edition, 1990.

For administration, the composition may be formulated readily by combining the peptide of SEQ ID No. 1, or a pharmaceutically acceptable salt or counterion thereof, with pharmaceutically acceptable carriers or excipients well known in the art. Such carriers enable the compositions of the invention to be formulated as solutions for injection by a patient to be treated.

Methods for treating a disease or disorder, including but not limited to, diabetes, a diabetes related disorder, obesity, or an obesity related disorder, may include administering a therapeutically effective amount of the peptide of SEQ ID No. 1, or a pharmaceutically acceptable salt or counterion thereof, as described herein. Treating a disease or disorder, including but not limited to, diabetes, a diabetes related disorder, obesity, or an obesity related disorder may also include prophylactically administering the peptide of SEQ ID No. 1, or a pharmaceutically acceptable salt or counterion thereof, to prevent diabetes, a diabetes related disorder, obesity, or an obesity related disorder in a subject at risk of developing diabetes, a diabetes related disorder, obesity or an obesity related disorder.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

The term "diabetes related disorders" should be understood to mean disorders that are associated with, caused by, or result from diabetes. Examples of diabetes related disorders include retinal damage, kidney disease, and nerve damage.

The compositions or pharmaceutical compositions described herein may be administered to a subject by any suitable means. Non-limiting examples of methods of administration include, among others, administration as a liquid or solution via subcutaneous injection, or other forms of injection.

Pharmaceutical compositions suitable for administration include compositions where the active ingredients are contained in an amount effective to achieve its intended purpose. In some embodiments, a therapeutically effective amount of a compound is an amount effective to treat diabetes, or a diabetes-related disorder, for example, in a mammalian subject (e.g., a human). The therapeutically effective amount of the peptide of SEQ ID No. 1, or a pharmaceutically acceptable salt or counterion thereof, required will depend on the route of administration, the type of animal, including human, being treated, and the physical characteristics of the specific animal under consideration.

The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1).

The pharmaceutical compositions of the present invention may be manufactured in a manner that is itself known, e.g., by means of conventional mixing, blending, dissolving, lyophilization, filtration, aseptic filling, and finishing.

In another embodiment the pharmaceutical compositions are prepared by standard sterile processing methods, which may include solution preparation, aseptic filtration, filling, finishing and lyophilization. In a class of this embodiment the pharmaceutical compositions are prepared by aseptic filtration, filling and finishing of a ready to use solution. An embodiment of this process is filling into a stoppered vial.

The pharmaceutical compositions obtained by the processing methods of the present invention may be filled into vials, syringes or cartridges.

In another embodiment of the present invention, the pharmaceutical compositions of the present invention are prepared by standard sterile processing methods, dry blending without the use of a granulation step.

The steps involved in the processing method comprise:
(1) Water or a custom solvent is charged to a suitable vessel and stirring is initiated;
(2) Each of the following ingredients is added one at a time, visually confirming dissolution before adding the next ingredient: buffer(s), anti-oxidant(s), tonicity agent(s), and antimicrobial agent(s);
(3) The pH of the formulation is measured and adjusted to pH 7.2;
(4) Then the peptide of SEQ I.D. NO. 1, or a pharmaceutically acceptable salt or counterion thereof, is added and dissolved by gently stirring.
(5) The pH is checked and adjusted to pH 7.1;
(6) Then water is added to the formulation to the desired final weight or volume;

(7) The formulation is conveyed through sterilizing grade filters and collected into an intermediate vessel;
(8) The formulation is filled into a 2 mL or 3 mL vial; and
(9) The vial is stoppered and capped with aluminum over the seal.

Alternatively, the steps involved in the processing method also comprise:
(1) Water or a custom solvent is charged to a suitable vessel and stirring is initiated;
(2) The following ingredients is added, one at a time, visually confirming dissolution before adding the next ingredient: buffer(s), antioxidant(s), tonicity agent(s), and antimicrobial agent(s);
(3) The pH of the formulation is adjusted to pH 7.3;
(4) The peptide of SEQ I.D. NO. 1, or a pharmaceutically acceptable salt or counterion thereof, is added and dissolved by gently stirring;
(5) Alternatively, the peptide is weighed into a suitable weighment vessel, then a portion of the formulation is charged to the weighment vessel to give a wetted slurry of the peptide which is poured into the formulation vessel;
(6) The pH of the solution is adjusted to pH 7.1;
(7) Water is added to the formulation to the desired final weight or volume;
(8) The formulation is collected in an intermediate vessel;
(9) The formulation is sterilized through redundant sterilizing grade filters into a filling manifold;
(10) The formulation into 3 mL cartridges; and
(11) The cartridges are then sealed with a combination stopper and over seal.

Alternatively, all of the excipients are added to the cartridge, and water or a custom solvent is added, and the mixture is lyophilized, followed by reconstitution with a solvent prior to injection.

Alternatively, all of the excipients are added to the cartridge, and water or a custom solvent is added prior to injection.

Alternatively, the peptide of SEQ I.D. NO. 1, or a pharmaceutically acceptable salt or counterion thereof, is added to the cartridge and a custom diluent, such as but not limited to the custom diluent of Example 2 or Example 3, is added to the cartridge prior to injection.

The present invention also provides methods for treating diabetes, or a diabetes-related disorder, by injecting into a host in need of such treatment a therapeutically effective amount of one of the pharmaceutical compositions of the present invention. In another embodiment the host in need of such treatment is a human. In another embodiment, the host in need of such treatment is an adult. In another embodiment, the host in need of such treatment is a child.

In another embodiment the pharmaceutical composition is in the dosage form of a solid formulation to which water may be added. In another embodiment the pharmaceutical composition is in the dosage form of a liquid formulation to which water may be added. In another embodiment the pharmaceutical composition is in the dosage form of a solution. In another embodiment the pharmaceutical composition is in the dosage form of a solution in water for subcutaneous injection.

The pharmaceutical compositions may be administered once-daily (QD), twice-daily (BID), or thrice-daily (TID), or multiple doses over several days for multi day treatment. In another embodiment, the pharmaceutical composition may be administered once daily for 6-10 days.

The following examples further describe and demonstrate embodiments within the scope of the present invention. The examples are given solely for the purpose of illustration and are not intended to be construed as limitations of the present invention as many variations thereof are possible without departing from the spirit and scope of the invention.

GENERAL EXAMPLE

Composition of the peptide of SEQ ID No. 1, or a pharmaceutically acceptable salt or counterion thereof, for constitution with a solvent or a custom solvent; or after constitution with a custom diluent

| Component | Unit Formula Range (mg/mL) after constitution with solvent or a custom solvent | Weight % Range (w/v) after constitution with a solvent or a custom solvent | Weight % Range (w/v) before constitution with a solvent or custom solvent |
| --- | --- | --- | --- |
| Peptide of SEQ. ID NO. 1, or a pharmaceutically acceptable salt or counterion thereof | about 0.1-10 mg/mL | about 0.01%-1% | about 0.1%-56% |
| Buffer, such as L-histidine | about 0.2-15 mg/mL | about 0.01-1.5% | about 0.1%-46% |
| One or more Anti-oxidants (such as L-Methionine and/or EDTA) | about 0.05-5 mg/mL | about 0.05-0.5% | about 0.1%-38% |
| Tonicity Agent (such as sucrose and/or propylene glycol) | about 10-60 mg/mL | about 1-6 % | about 14%-88% |
| Anti-microbial agent (such as benzyl alcohol, phenol and/or m-cresol) | about 8-30 mg/mL | about 0.8%-3% | about 9.6%-99.7% |
| Water for injection (or a custom solvent or a custom dilluent) | q.s. to 1 mL | q.s. to 100% | None |

-continued

| Component | Unit Formula Range (mg/mL) after constitution with solvent or a custom solvent | Weight % Range (w/v) after constitution with a solvent or a custom solvent | Weight % Range (w/v) before constitution with a solvent or custom solvent |
|---|---|---|---|
| Base (such as 1N sodium hydroxide solution) | q.s. to pH 7.1 | as needed | as needed |
| Acid (such as 1N hydrochloric acid) | q.s. to pH 7.1 | as needed | as needed |
| Total | 100% | 100% | 100% |
| pH (constitution with solvent | about 6.7-8.4 | about 6.7-8.4 | about 6.7-8.4 |

General Method of Manufacture 1:

Water is charged to a suitable vessel and stirring is initiated. Each of the following ingredients is added, one at a time, visually confirming dissolution before adding the next ingredient: L-histidine, L-methionine, EDTA, sucrose and benzyl alcohol. The pH of the formulation is measured and adjusted to a target of pH 7.2. Then the peptide of SEQ I.D. NO. 1 is added and dissolved by gently stirring. Once the peptide is fully dissolved, the pH is checked and adjusted to pH 7.1. Then water is added to the formulation to the desired final weight. The formulation is conveyed by appropriate means, such as a peristaltic pump, through sterilizing grade filters and collected into an intermediate vessel. The formulation is then filled into a suitable vial, stoppered and capped with aluminum over the seal.

General Method of Manufacture 2:

Water is charged to a suitable vessel and stirring is initiated. Each of the following ingredients is added, one at a time, visually confirming dissolution before adding the next ingredient: L-histidine, L-methionine, EDTA, sucrose, and benzyl alcohol. The pH of the formulation is measured and adjusted to pH 7.3. Then the peptide of SEQ I.D. NO. 1 is added and dissolved by gently stirring. The transfer of peptide is aided by weighing the powder into a suitable weighment vessel, then charging a portion of the formulation to the weighment vessel to create a wetted slurry of the peptide, and pouring the slurry into the formulation vessel. The weighment vessel should be rinsed appropriately. Once the peptide is fully dissolved, the pH is checked and adjusted to pH 7.1. Then water is added to the formulation to the desired final weight. The formulation is then conveyed by a peristaltic pump through an appropriate bio burden reduction filter and collected in an intermediate vessel. Then, by a time/pressure mechanism, the formulation is sterilized through redundant sterilizing grade filters into a filling manifold, and the filling of the formulation into 3 mL cartridges, suitable for use in a pen injector device. The cartridges are filled in two stages, where filling is stopped at the second stage through control by a laser indicator. The cartridges are then sealed with a combination stopper and over seal.

EXAMPLE 1

Approximately 170 g of water for injection was added to a 250 mL beaker with a stir bar. The following additions were performed sequentially, with complete dissolution confirmed visually before adding the next ingredient. Between the addition of sucrose and peptide of SEQ. ID NO. 1, mixing was stopped and the pH was confirmed to be between 7 and 8. After addition and dissolution of the peptide, the pH was adjusted to 7.2+/−0.05 with 1 N HCl. Water for injection was added to give a final batch net weight of 201.6 g. The batch was sterile filtered using a 250 mL vacuum drive filtration assembly with a 0.22 um filter. The batch was then aseptically filled in vials using a repeater pipet and manually stoppered.

| Component | Amount | Unit formula |
|---|---|---|
| Disodium EDTA Dihydrate | 0.0761 g | 0.37 mg/mL |
| Benzyl Alcohol | 3.61 g | 18 mg/mL |
| L-Histidine | 1.56 g | 7.75 mg/mL |
| L-Methionine | 0.300 g | 1.49 mg/mL |
| Sucrose | 10.0 g | 50 mg/mL |
| peptide of SEQ. ID NO. 1 | 0.440 g | 2.00 mg/mL |
| Base (such as 1N sodium hydroxide solution) | q.s. to pH 7.1 | As needed |
| Acid (such as 1N hydrochloric acid) | q.s. to pH 7.1 | As needed |
| Water for injection | q.s. to 201.6 g | q.s. to 1 mL |

EXAMPLE 2

A custom diluent was prepared as follows. 1502.4 g of water for injection was added to a 3 L vessel, and stirring was initiated. All of the following components were added, one at a time, and mixed until dissolved before adding the next component. After dissolution of all components, the pH was confirmed to be between 7 and 8. Water for injection was added to give a final batch weight of 2041.4 g

| Component | Amount | Unit formula |
|---|---|---|
| Disodium EDTA Dihydrate | 0.745 g | 0.37 mg/mL |
| Benzyl Alcohol | 36.0 g | 18 mg/mL |
| L-Histidine | 15.5 g | 7.75 mg/mL |
| L-Methionine | 3.00 g | 1.49 mg/mL |
| Sucrose | 100.4 g | 50 mg/mL |
| Water for injection | q.s. to 20411 g | q.s. to 1 mL |

A 3 mg/mL preparation of peptide of SEQ. ID NO. 1 was prepared by adding 425.3 g of a custom diluent to a 1 L vessel with a stir bar. Then 3.12 g of the peptide of SEQ. ID NO. 1 was slowly added to the vessel, followed by stirring to dissolve. Then the pH was checked and confirmed to be pH 7.2+/−0.05.

The 3 mg/mL preparation of the peptide of SEQ. ID NO. 1 and the custom diluent were each sterile filtered and transferred into sterile glass vessels. The solutions were aseptically filled at 1.1 mL into a 2 mL vial, stoppered and capped with an aluminum overseal. Then cartridges were prepared by inserting a plunger into each cartridge, followed by filling with 3.036 g of formulation or custom diluent, and sealed with a crimped Combiseal.

EXAMPLE 3

A custom diluent was prepared as follows. 2396.5 g of water for injection was added to a 4 L vessel and stirring was initiated. All of the following components were added and mixed to dissolve. After dissolution of all components, the pH was confirmed to be between 7 and 8. Then water for injection was added to give a final batch weight of 3039.5 g

| Component | Amount | Unit formula |
|---|---|---|
| L-Histidine | 23.2 g | 7.73 mg/mL |
| L-Methionine | 4.364 g | 1.45 mg/mL |
| Disodium EDTA Dihydrate | 0.988 g | 0.33 mg/mL |
| Sucrose | 90.09 g | 30 mg/mL |
| Water for injection | q.s. to 3039.5 g | q.s. to 1 mL |

EXAMPLE 4

Self-associated or aggregated peptides scatter light due to their size, shape, color and reflectivity. Measurement of the light scattered from a beam focused on a sample at a 90 degree angle is a method of detecting the presence of self-associated or aggregated peptides in liquid samples, where more extensively aggregated peptides are expected to scatter more light. This measurement may be used to screen formulation conditions and to detect the presence of sub-visible species. A Spectramax m5e UV/Visible Spectrophotometer in Fluorescence mode was used to illuminate a sample with 600 nm wavelength light in a 10 mm×2 mm quartz cuvette and a fluorescence detector at 90 degree angle to the incident light was used to detect the amount of light scattered at that wavelength. The output of the measurement was reported in RFU by the instrument. Measurement of a linear calibration set of Turbidity standards shows a linear correlation between the Relative Fluorescence Units (RFU) output and Nephelometric Turbidity Units (NTU).

| Turbidity standard (NTU) | RFU (n = 3) |
|---|---|
| 0 | 28 ± 1.1 |
| 0.2 | 133 ± 14 |
| 0.4 | 213 ± 18 |
| 0.6 | 295 ± 14 |
| 0.8 | 325 ± 5.5 |
| 1 | 461 ± 1.2 |

Solutions of the peptide of Sequence ID No. 1 were prepared with antimicrobial agents in concentrations known in the art to have antimicrobial effectiveness. After overnight storage at 2-8 Celsius, the formulations containing meta cresol and phenol alone were found to be visually cloudy, while the benzyl alcohol formulation remained visually clear.

Formulations 4-1 to 4-18 of the peptide of SEQ. ID NO. 1 were prepared as shown in Tables 1, 2 and 3 below. The formulations were stored at controlled room temperature for 2 weeks protected from light, then the turbidity was analyzed by the procedure described above. The turbidity, reported as RFU, was found to increase significantly for phenol and meta-cresol containing compositions relative to benzyl alcohol containing formulations.

TABLE 1

| Formulation | 4-1 | 4-2 | 4-3 | 4-4 | 4-5 | 4-6 | 4-7 | 4-8 | 4-9 | 4-10 |
|---|---|---|---|---|---|---|---|---|---|---|
| Peptide of SEQ. ID NO. 1 | 0.6 | 0.6 | 0.6 | 0.6 | 0.6 | 0.6 | 0.6 | 0.6 | 0.6 | 0.6 |
| L-histidine (mg/mL) | 7.64 | 7.64 | 7.64 | 7.64 | 7.64 | 7.64 | 7.64 | 7.64 | 7.64 | 7.64 |
| phenol (mg/mL) | 1 | 2 | 3 | 4 | 5 | 8 | 10 | 15 | 20 | 40 |
| pH | 7.0 | 7.0 | 7.0 | 7.0 | 7.0 | 7.0 | 7.0 | 7.0 | 7.0 | 7.0 |
| Turbidity (RFU) | 140 | 78 | 211 | 235 | 552 | 931 | 1659 | 2029 | 2605 | 2997 |

TABLE 2

| Formulation | 4-11 | 4-12 |
|---|---|---|
| Peptide of SEQ. ID NO. 1 | 0.6 | 0.6 |
| L-histidine (mg/mL) | 7.64 | 7.64 |
| Meta-cresol (mg/mL) | 2 | 3 |
| pH | 7.0 | 7.0 |
| Turbidity (RFU) | 1320 | 5135 |

TABLE 3

| Formulation | 4-13 | 4-14 | 4-15 | 4-16 | 4-17 | 4-18 |
|---|---|---|---|---|---|---|
| Peptide of SEQ. ID NO. 1 | 0.6 | 0.6 | 0.6 | 0.6 | 0.6 | 0.6 |
| L-histidine (mg/mL) | 7.64 | 7.64 | 7.64 | 7.64 | 7.64 | 7.64 |
| Benzyl alcohol (mg/mL) | 3.6 | 7.2 | 11 | 14 | 18 | 22 |
| pH | 7.0 | 7.0 | 7.0 | 7.0 | 7.0 | 7.0 |
| Turbidity (RFU) | 90 | 97 | 66 | 70 | 41 | 182 |

EXAMPLE 5

The relative physical stability of the peptide of SEQ. ID NO. 1, was evaluated under stressed conditions using the addition of NaCl to increase ionic strength to accelerate aggregation.

Formulations 5-1 to 5-12 containing the peptide of SEQ ID NO. 1 for evaluating the effect of increasing ionic strength were prepared as shown in Tables 4, and 5 below. The formulations were stored at 2-8 Celsius in the dark for 20 days, and then the light scattered by a sample was determined by placing the formulation in a fluorescence cuvette with a 2 mm×10 mm path length and analyzing the sample in a Spectramax Me5 fluorescence spectrophotometer, illuminating the sample with 600 nm light and reporting relative fluorescence units (RFU) of light with a 598 nm wavelength by a detector at a 90 degree angle to the incident beam. Five replicate measurements on the same sample were averaged and reported. The resolution of the spectrophotometer is 2 nm.

Formulations containing benzyl alcohol did not increase in turbidity when sodium chloride was titrated in, while formulations without benzyl alcohol significantly increased in turbidity, demonstrating improved stability and decreased aggregation propensity of the peptide of SEQ ID No. 1 in the presence of benzyl alcohol.

TABLE 4

| Formulation | Unit formula (mg/mL) | | | | | |
| --- | --- | --- | --- | --- | --- | --- |
| | 5-1 | 5-2 | 5-3 | 5-4 | 5-5 | 5-6 |
| Peptide of SEQ. ID NO. 1 (mg/mL) | 1.00 | 1.00 | 1.00 | 1.00 | 1.00 | 1.00 |
| Histidine | 7.76 | 7.76 | 7.76 | 7.76 | 7.76 | 7.76 |
| Methionine | 1.49 | 1.49 | 1.49 | 1.49 | 1.49 | 1.49 |
| EDTA Na$_2$ | 1.86 | 1.86 | 1.86 | 1.86 | 1.86 | 1.86 |
| Sucrose | 50.0 | 50.0 | 50.0 | 50.0 | 50.0 | 50.0 |
| Benzyl Alcohol | 20.0 | 20.0 | 20.0 | 20.0 | 20.0 | 20.0 |
| NaCl (mM) | 14.0 | 24.0 | 34.0 | 54.0 | 104 | 122 |
| pH | 6.9 | 6.9 | 6.9 | 6.9 | 6.9 | 6.9 |
| RFU | 114 +/− 7 | 125 +/− 13 | 114 +/− 20 | 126 +/− 3 | 206 +/− 10 | 306 +/− 2 |

TABLE 5

| Formulation | Unit formula (mg/mL) | | | | | |
| --- | --- | --- | --- | --- | --- | --- |
| | 5-7 | 5-8 | 5-9 | 5-10 | 5-11 | 5-12 |
| Peptide of SEQ. ID NO. 1 | 1.00 | 1.00 | 1.00 | 1.00 | 1.00 | 1.00 |
| Histidine | 7.76 | 7.76 | 7.76 | 7.76 | 7.76 | 7.76 |
| Methionine | 1.49 | 1.49 | 1.49 | 1.49 | 1.49 | 1.49 |
| EDTA Na$_2$ | 1.86 | 1.86 | 1.86 | 1.86 | 1.86 | 1.86 |
| Sucrose | 50.0 | 50.0 | 50.0 | 50.0 | 50.0 | 50.0 |
| Benzyl Alcohol | 0 | 0 | 0 | 0 | 0 | 0 |
| NaCl (mM) | 12.0 | 22.0 | 32.0 | 52.0 | 102 | 122 |
| pH | 7.0 | 7.0 | 7.0 | 7.0 | 7.0 | 7.0 |
| RFU | 176 +/− 4 | 230 +/− 34 | 205 +/− 4 | 2464 +/− 137 | 23371 +/− 454 | 26006 +/− 289 |

EXAMPLE 6

Shaking or mild agitation was also as a stress to assess the relative physical stability of the peptide of SEQ ID NO. 1 formulations. Formulations 6-1 to 6-6 containing the peptide of SEQ ID NO 1, shown in Table 6 below, were prepared and filled into 3 mL cartridges, sealed and stored at 2-8 Celsius for 6 days. The cartridges were either: 1) stored unshaken or 2) placed on a Clay Adams Nutator orbital shaker and shaken for 6 days. On the 6$^{th}$ day, the turbidity of formulations 6-1 to 6-6 was measured.

At a concentration of 3 mg/mL of the peptide of SEQ ID NO 1, the formulations without benzyl alcohol (6-1, and 6-4) had significantly increased turbidity compared to the formulations with benzyl alcohol, indicating aggregation in the formulations without benzyl alcohol. Additionally, the turbidity in the shaken formulations without benzyl alcohol was higher than the turbidity of the unshaken samples, indicating that the peptide of SEQ ID NO 1 is sensitive to shaking. However, there was no significant increase in the turbidity of the benzyl alcohol containing formulations under shaken or unshaken conditions.

TABLE 6

| Formulation | 6-1 | 6-2 | 6-3 | 6-4 | 6-5 | 6-6 |
| --- | --- | --- | --- | --- | --- | --- |
| Peptide | 0.1 | 0.1 | 0.1 | 3 | 3 | 3 |
| Histidine | 7.815 | 7.815 | 7.815 | 7.815 | 7.815 | 7.815 |
| EDTA | 0.3734 | 0.3734 | 0.3734 | 0.3734 | 0.3734 | 0.3734 |
| Methionine | 1.545 | 1.545 | 1.545 | 1.545 | 1.545 | 1.545 |
| Sucrose | 50.08 | 50.08 | 50.08 | 50.08 | 50.08 | 50.08 |
| Benzyl Alcohol (mg/mL) | 0 | 20.135 | 38 | 0 | 20.135 | 38 |
| Turbidity (RFU) 6 days 2-8° C. Shaken | 67 | 75 | 86 | 1771 | 168 | 164 |
| Turbidity (RFU) 6 days, 2-8° C., Not Shaken | 98 | 129 | 120 | 896 | 146 | 163 |

What is claimed is:

1. A pharmaceutical composition comprising:
   1) about 0.1%-56% by weight of the peptide of SEQ ID NO. 1, or a pharmaceutically acceptable salt or counterion thereof;
   2) about 9.6%-99.7% by weight of an anti-microbial agent,
   3) about 0.1% -46% by weight of a buffer;
   4) about 0.1% -38% by weight of an anti-oxidant; and
   5) about 14% -88% by weight of a tonicity agent;
   before constitution with a solvent, or a custom solvent, wherein
   the anti-microbial agent is benzyl alcohol;
   the buffer is L-histidine;
   the tonicity agent is selected from:
   1) propylene glycol, and
   2) sucrose; and
   the anti-oxidant is selected from:
   1) L-methionine,
   2) ethylenediamine tetra acetic acid or a salt and/or hydrate thereof, and
   3) a combination of L-methionine and ethylenediamine tetra acetic acid, or a salt and/or hydrate thereof.

2. The pharmaceutical composition of claim 1 wherein the tonicity agent is sucrose; and
the anti-oxidant is a combination of L-methionine and ethylenediamine tetra acetic acid, or a salt and/or hydrate thereof.

3. The pharmaceutical composition of claim 1 wherein the pharmaceutical composition is constituted with a solvent, or a custom solvent.

4. The pharmaceutical composition of claim 1 comprising:
   1) about 0.6%-24% by weight of the peptide of SEQ ID No. 1, or a pharmaceutically acceptable salt or counterion thereof;
   2) about 10.2%-98.8 by weight of an anti-microbial agent;
   3) about 1.2%-43% by weight of a buffer;
   4) about 0.1% -21% by weight of an anti-oxidant; and
   5) about 34%-79% by weight of a tonicity agent,
   before constitution with a solvent, or a custom solvent, wherein
   the anti-microbial agent is benzyl alcohol;
   the buffer is L-histidine;
   the tonicity agent is selected from:
   1) propylene glycol, and
   2) sucrose; and
   the anti-oxidant is selected from:
   1) L-methionine,
   2) ethylenediamine tetra acetic acid or a salt and/or hydrate thereof, and
   a combination of L-methionine and ethylenediamine tetra acetic acid, or a salt and/or hydrate_thereof.

5. The pharmaceutical composition of claim 4 wherein the tonicity agent is sucrose; and
the anti-oxidant is a combination of L-methionine and ethylenediamine tetra acetic acid, or a salt and/or hydrate thereof.

6. The pharmaceutical composition of claim 4 additionally comprising water.

7. The pharmaceutical composition of claim 1 comprising:
   1) about 1.3%-17% by weight of the peptide of SEQ ID No. 1, or a pharmaceutically acceptable salt or counterion thereof;
   2) about 22%-94% by weight of an anti-microbial agent;
   3) about 5.6%-36% by weight of a buffer;
   4) about 1.5-11% by weight of an anti-oxidant; and
   5) about 42%-72% by weight of a tonicity agent,
   before constitution with a solvent, or a custom solvent, wherein the anti-microbial agent is benzyl alcohol;
the buffer is L-histidine;
the tonicity agent is selected from;
1) propylene glycol, and
2) sucrose; and
the anti-oxidant is selected from:
1) L-methionine,
2) ethylenediamine tetra acetic acid or a salt and/or hydrate thereof, and a combination of L-methionine and ethylenediamine tetra acetic acid or a salt and/or hydrate thereof.

8. The pharmaceutical composition of claim 7 wherein the tonicity agent is sucrose; and the anti-oxidant is a combination of L-methionine and ethylenediamine tetra acetic acid or a salt and/or hydrate thereof.

9. The pharmaceutical composition of claim 7 additionally comprising water.

10. The pharmaceutical composition of claim 1 comprising:
1) about 2%-4% by weight of the peptide of SEQ ID No. 1, or a pharmaceutically acceptable salt or counterion thereof;
2) about 28%-32% by weight of benzyl alcohol;
3) about 12%-14% by weight of L-histidine;
4) about 48%-52% by weight of sucrose;
5) about 2%-3% by weight of L-methionine; and
6) about 0.01%-0.5% by weight of ethylenediamine tetra acetic acid, or a salt and/or hydrate thereof,
before constitution with a solvent, or a custom solvent.

11. The pharmaceutical composition of claim 10 additionally comprising water.

12. A method of treating diabetes, a diabetes related disorder, obesity or an obesity related disorder, in a human in need thereof comprising administering to the human a pharmaceutical composition of claim 1.

13. The pharmaceutical composition comprising:
1) about 0.01%-1% by weight of the peptide of SEQ ID NO. 1, or a pharmaceutically acceptable salt or counterion thereof;
2) about 0.8% -3% by weight of an anti-microbial agent;
3) about 0.01%-1.5% by weight of a buffer;
4) about 0.05%-0.5% by weight of an anti-oxidant; and
5) about 1%-6% by weight of a tonicity agent;
after constitution with a solvent, or a custom solvent,
wherein
the anti-microbial agent is benzyl alcohol;
the buffer is L-histidine;
the tonicity agent is selected from:
1) propylene glycol, and
2) sucrose; and
the anti-oxidant is selected from:
1) L-methionine,
2) ethylenediamine tetra acetic acid or a salt and/or hydrate thereof, and
3) a combination of L-methionine and ethylenediamine tetra acetic acid, or a salt and/or hydrate thereof.

14. The pharmaceutical composition of claim 13 wherein the tonicity agent is sucrose; and the anti-oxidant is a combination of L-methionine and ethylenediamine tetra acetic acid, or a salt and/or hydrate thereof.

15. The pharmaceutical composition of claim 14 wherein the solvent is water.

16. The pharmaceutical composition of claim 13 wherein the solvent is water.

17. The pharmaceutical composition of claim 13 comprising:
1) about 0.05%-0.4% by weight of the peptide of SEQ ID No. 1, or a pharmaceutically acceptable salt or counterion thereof;
2) about 1.3%-2.5% by weight of an anti-microbial agent;
3) about 0.1%-10.9% by weight of a buffer;
4) about 0.15%-0.3% by weight of an anti-oxidant; and
5) about 2%-5% by weight of a tonicity agent,
after constitution with a solvent, or a custom solvent,
wherein
the anti-microbial agent is benzyl alcohol;
the buffer is L-histidine;
the tonicity agent is selected from:
1) propylene glycol, and
2) sucrose; and
the anti-oxidant is selected from:
1) L-methionine,
2) ethylenediamine tetra acetic acid or a salt and/or hydrate thereof, and ps a combination of L-methionine and ethylenediamine tetra acetic acid, or a salt and/or hydrate thereof.

18. The pharmaceutical composition of claim 17 wherein the tonicity agent is sucrose; and the anti-oxidant is a combination of L-methionine and ethylenediamine tetra acetic acid, or a salt and/or hydrate thereof.

19. The pharmaceutical composition of claim 17 wherein the solvent is water.

20. The pharmaceutical composition of claim 13 comprising:
1) about 0.01%-2% by weight of the peptide of SEQ ID No. 1, or a pharmaceutically acceptable salt or counterion thereof;
2) about 1%-3% by weight of benzyl alcohol;
3) about 0.5%-1% by weight of L-histidine;
4) about 2%-4% by weight of sucrose;
5) about 0.01%-0.3% by weight of L-methionine; and
6) about 0.01%-0.3% by weight of ethylenediamine tetra acetic acid, or a salt and/or hydrate thereof,
after constitution with a solvent, or a custom solvent.

21. The pharmaceutical composition of claim 20 wherein the solvent is water.

* * * * *